US012268851B2

(12) United States Patent
Dahmani et al.

(10) Patent No.: US 12,268,851 B2
(45) Date of Patent: Apr. 8, 2025

(54) SYSTEMS AND METHODS FOR AUTOMATICALLY REMOVING A NEEDLE CAP OF AN AUTOINJECTOR

(71) Applicant: QuiO Technologies LLC, New York, NY (US)

(72) Inventors: Alexander Dahmani, New York, NY (US); Jared Schwartzentruber, Astoria, NY (US)

(73) Assignee: QuiO Technologies LLC, Miami, FL (US)

( * ) Notice: Subject to any disclaimer, the term of this patent is extended or adjusted under 35 U.S.C. 154(b) by 1228 days.

(21) Appl. No.: 17/041,968

(22) PCT Filed: Mar. 26, 2019

(86) PCT No.: PCT/US2019/024086
§ 371 (c)(1),
(2) Date: Sep. 25, 2020

(87) PCT Pub. No.: WO2019/191105
PCT Pub. Date: Oct. 3, 2019

(65) Prior Publication Data
US 2021/0138160 A1 May 13, 2021

Related U.S. Application Data

(60) Provisional application No. 62/648,770, filed on Mar. 27, 2018, provisional application No. 62/648,762, (Continued)

(51) Int. Cl.
*A61M 5/315* (2006.01)
*A61M 5/20* (2006.01)
(Continued)

(52) U.S. Cl.
CPC ...... *A61M 5/31528* (2013.01); *A61M 5/2033* (2013.01); *A61M 5/28* (2013.01);
(Continued)

(58) Field of Classification Search
CPC .............. A61M 5/3204; A61M 5/3232; A61M 2205/12; A61M 2205/123;
(Continued)

(56) References Cited

U.S. PATENT DOCUMENTS 5,219,099 A 6/1993 Spence et al.
8,591,463 B1 11/2013 Cowe
(Continued)

FOREIGN PATENT DOCUMENTS

EP 2 364 740 A1 9/2011
EP 2 727 617 A1 5/2014
(Continued)

OTHER PUBLICATIONS

International Search Report and Written Opinion dated Jun. 20, 2019 for International Application No. PCT/US2019/024085.
(Continued)

*Primary Examiner* — Shefali D Patel
*Assistant Examiner* — Nidah Hussain
(74) *Attorney, Agent, or Firm* — Wood, Phillips, Katz, Clark & Mortimer

(57) ABSTRACT

An autoinjector device includes a dose cassette having an outer container and a needle cap having a base with a diameter larger than the outer container of the dose cassette. The autoinjector device further includes a housing for receiving the dose cassette, a clasp mechanism configured to hold the dose cassette within the housing, and an actuator configured to move the dose cassette proximally within the housing after the dose cassette is secured within the housing. The movement of the dose cassette causes the base of the
(Continued)

needle cap to mechanically engage with a distal end of the housing, and the mechanical engagement between the base of the needle cap and the distal end of the housing causes the needle cap to separate from the dose cassette.

20 Claims, 28 Drawing Sheets

Related U.S. Application Data filed on Mar. 27, 2018, provisional application No. 62/648,772, filed on Mar. 27, 2018, provisional application No. 62/648,766, filed on Mar. 27, 2018.

(51) Int. Cl.
*A61M 5/28* (2006.01)
*A61M 5/32* (2006.01)

(52) U.S. Cl.
CPC .... *A61M 5/31525* (2013.01); *A61M 5/31558* (2013.01); *A61M 5/3202* (2013.01); *A61M 5/3204* (2013.01); *A61M 2205/12* (2013.01); *A61M 2205/14* (2013.01)

(58) Field of Classification Search
CPC ...... A61M 2205/14; A61M 5/20; A61M 5/24; A61M 5/2422; A61M 5/32; A61M 5/3202; A61M 2005/2006; A61M 2005/2403; A61M 2005/2433; A61M 2005/2437; A61M 2005/244; A61M 2005/2477; A61M 5/28; A61M 5/2033; A61M 5/31528

USPC ....................................................... 604/506
See application file for complete search history.

(56) References Cited

U.S. PATENT DOCUMENTS

| | | | |
|---|---|---|---|
| 2002/0049415 | A1 | 4/2002 | Fukuda |
| 2012/0035542 | A1* | 2/2012 | Pongprairochana .... A61M 5/20 604/110 |
| 2014/0012229 | A1* | 1/2014 | Bokelman ........... A61M 5/2033 604/154 |
| 2014/0058333 | A1 | 2/2014 | Cross et al. |
| 2016/0022914 | A1 | 1/2016 | Mounce et al. |
| 2016/0184519 | A1 | 6/2016 | Blundred et al. |
| 2016/0287815 | A1 | 10/2016 | Aoki et al. |

FOREIGN PATENT DOCUMENTS

| | | |
|---|---|---|
| WO | 2009/143255 A1 | 11/2009 |
| WO | WO 2017/089269 | 6/2017 |
| WO | WO 2018/009509 | 1/2018 |

OTHER PUBLICATIONS

International Search Report and Written Opinion dated Jun. 20, 2019 for International Application No. PCT/US2019/024086.
International Search Report and Written Opinion dated Jun. 20, 2019 for International Application No. PCT/US2019/024092.
Supplementary European Search Report issued Oct. 26, 2021 in European Patent Application No. EP 19 77 7728.

* cited by examiner

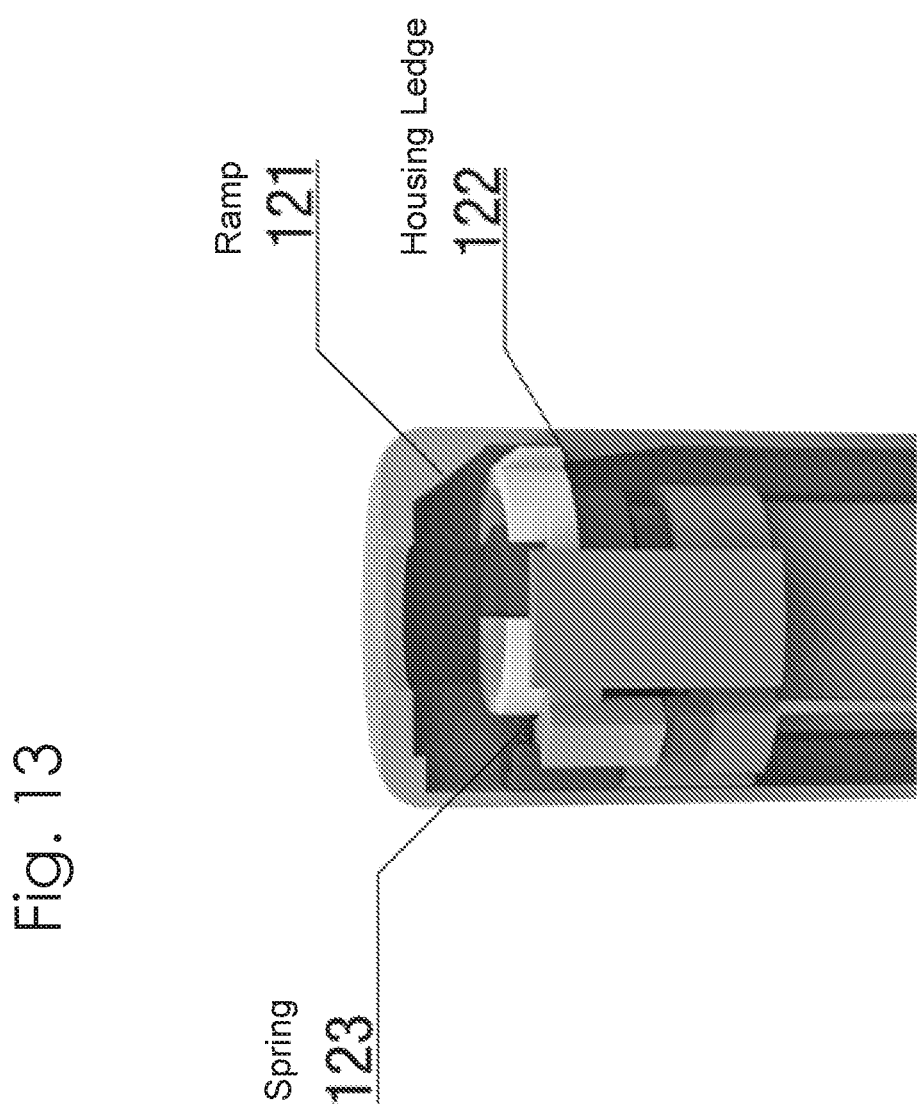

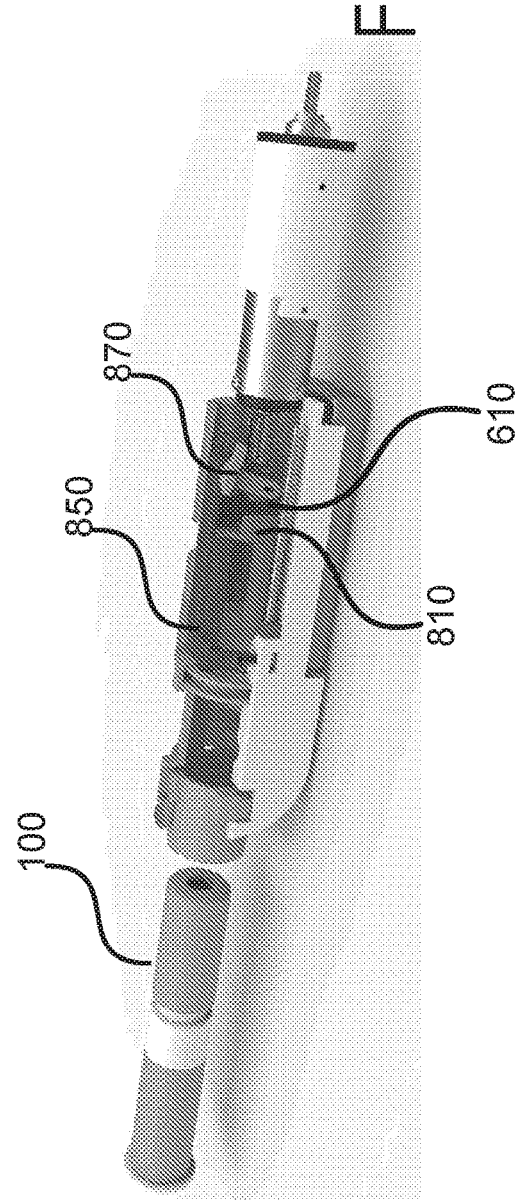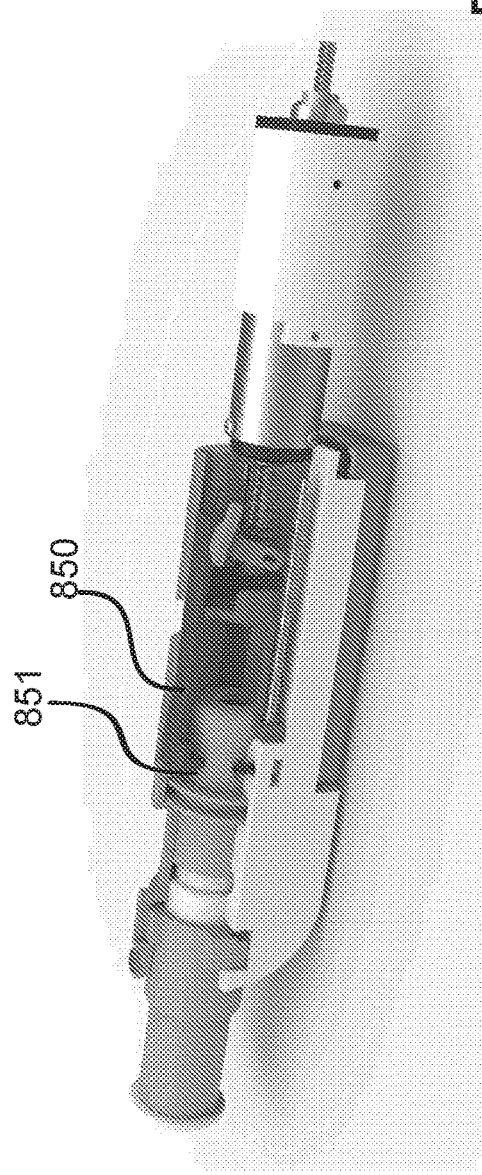

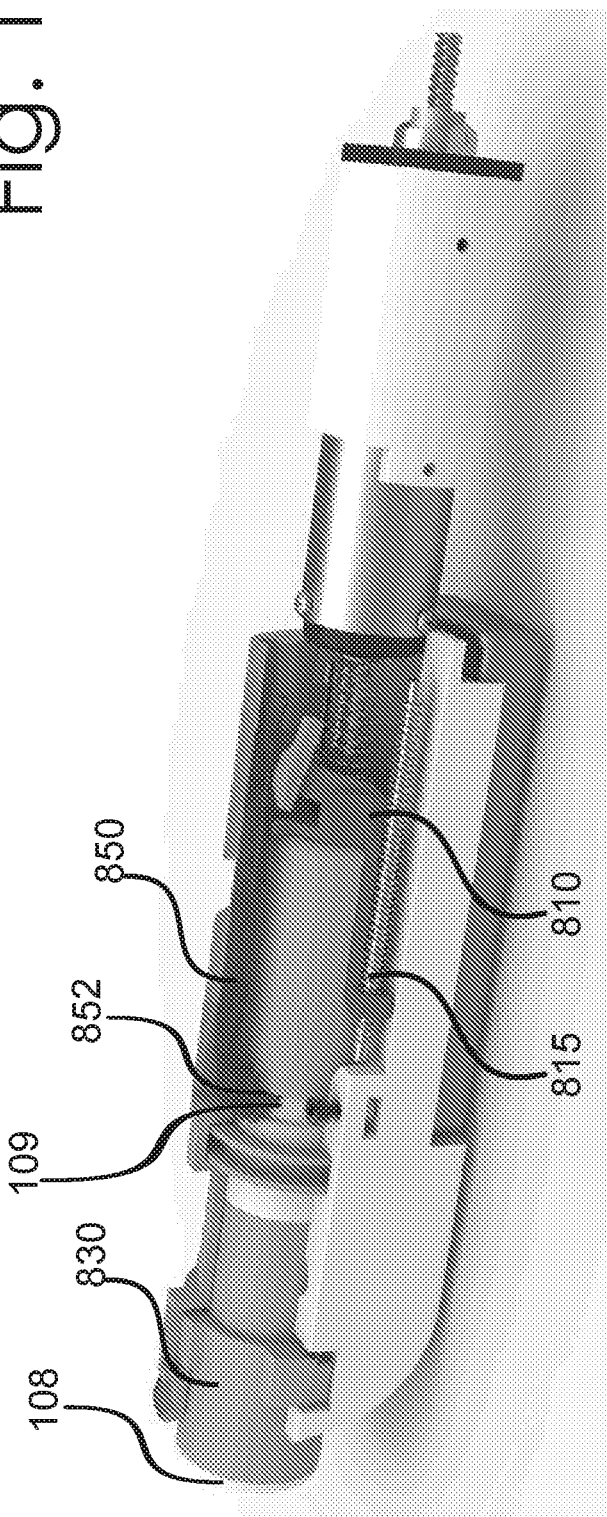

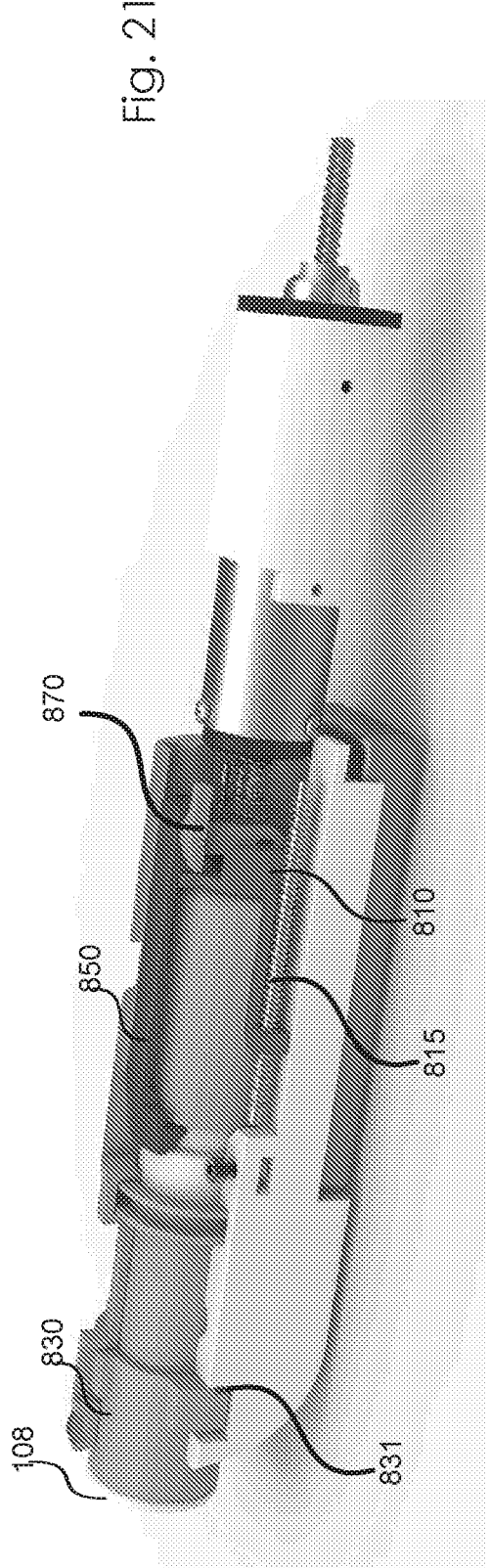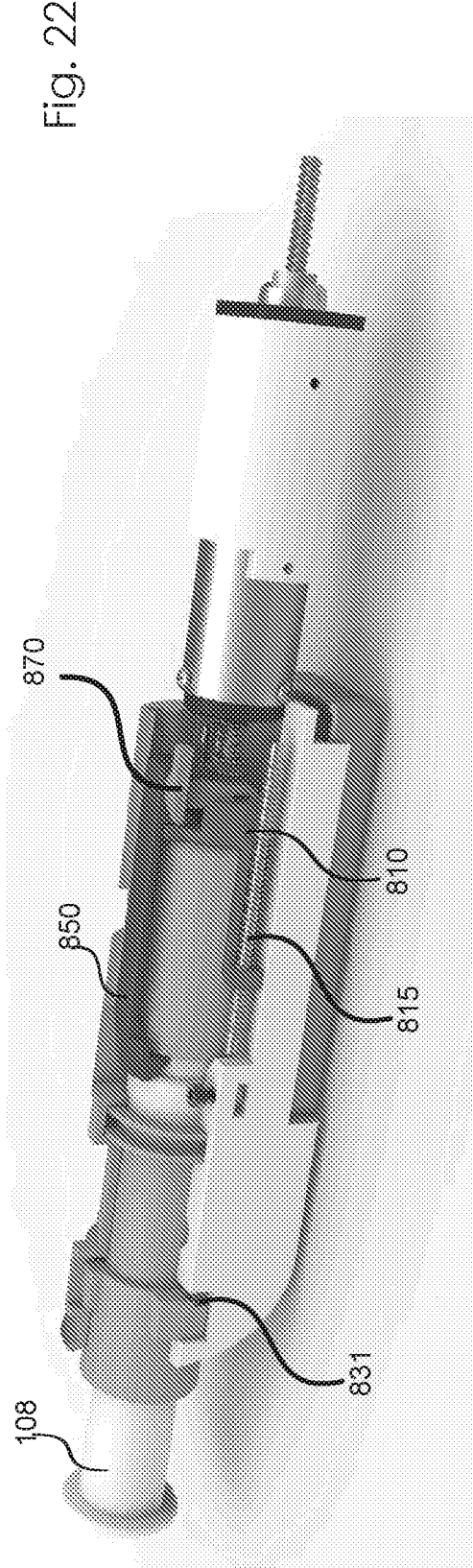

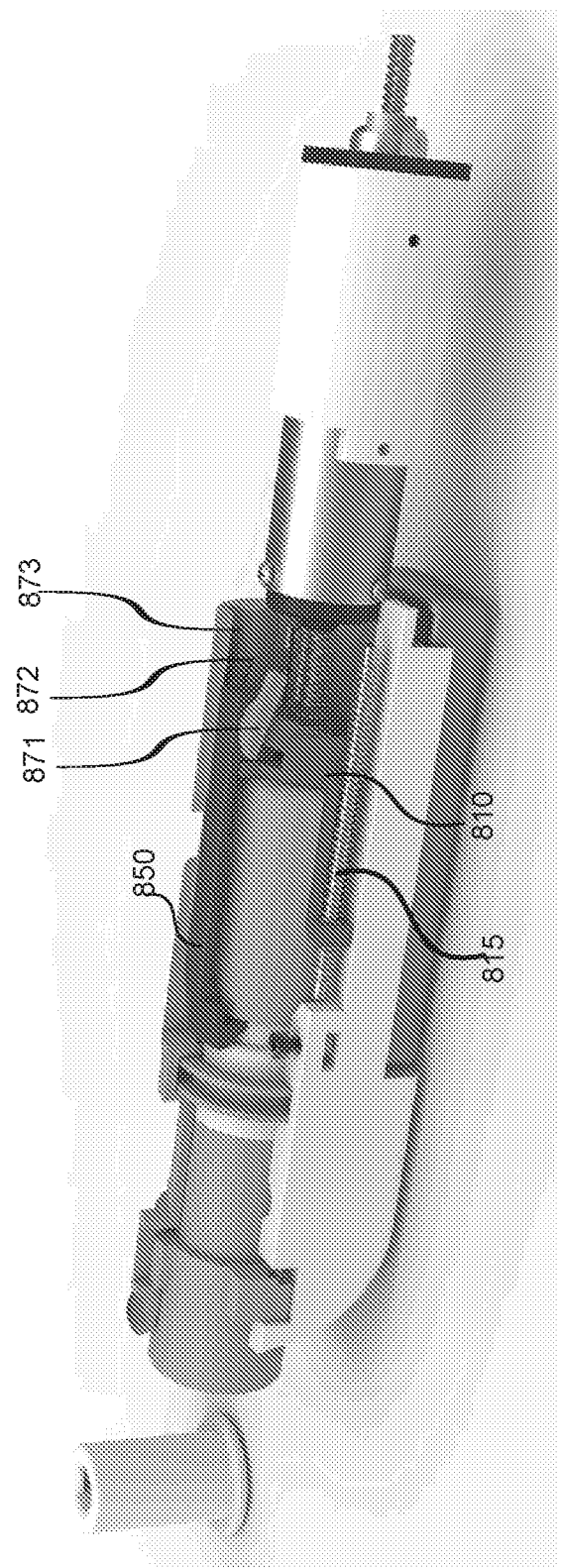
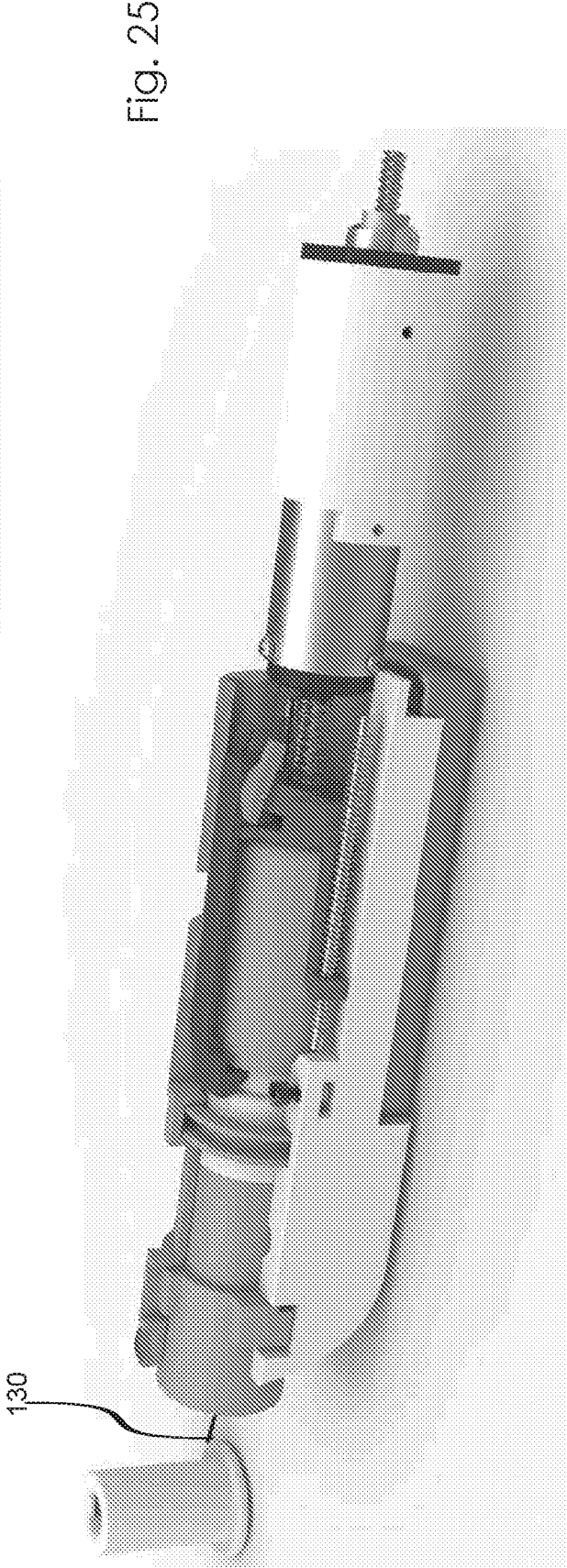
Fig. 24
Fig. 25

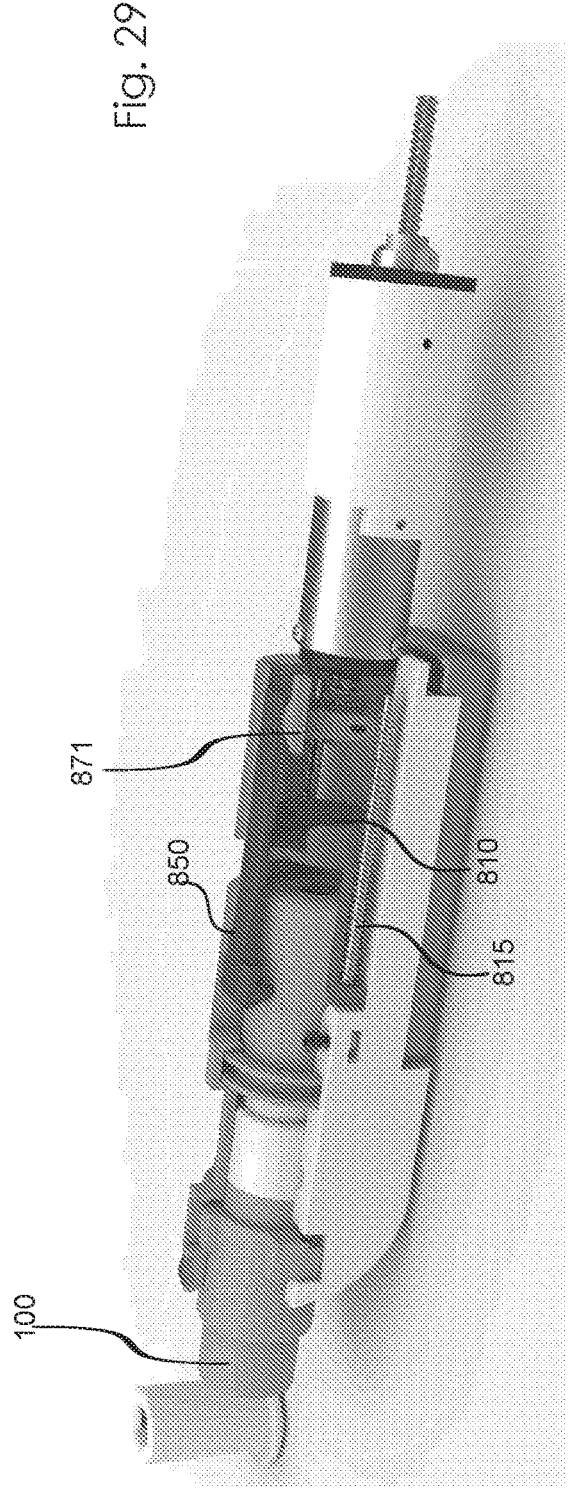
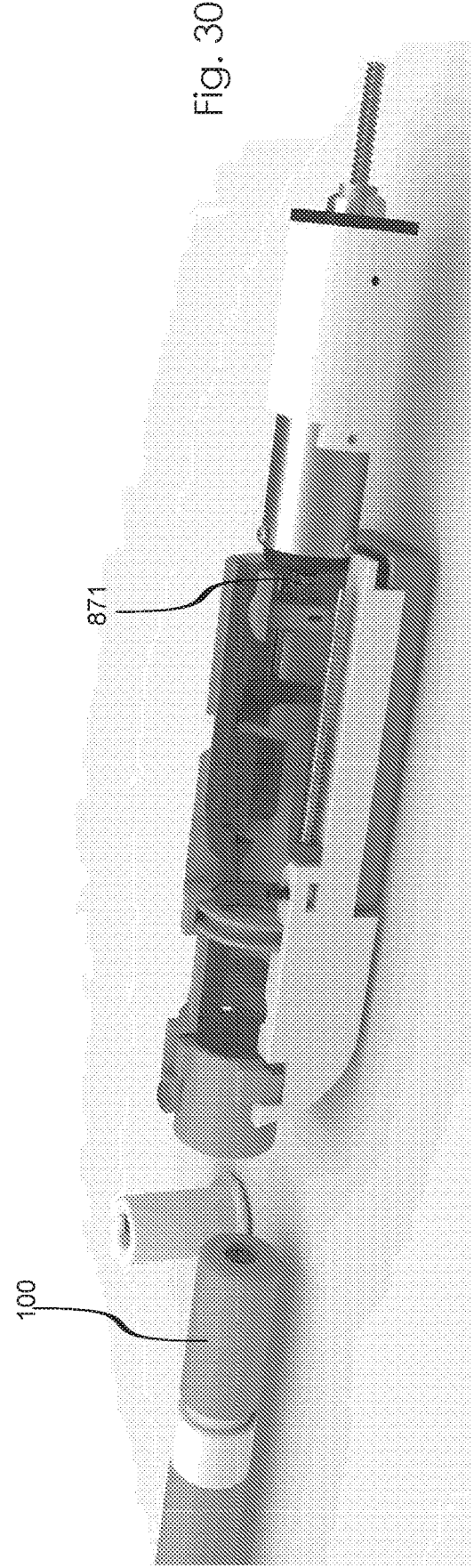

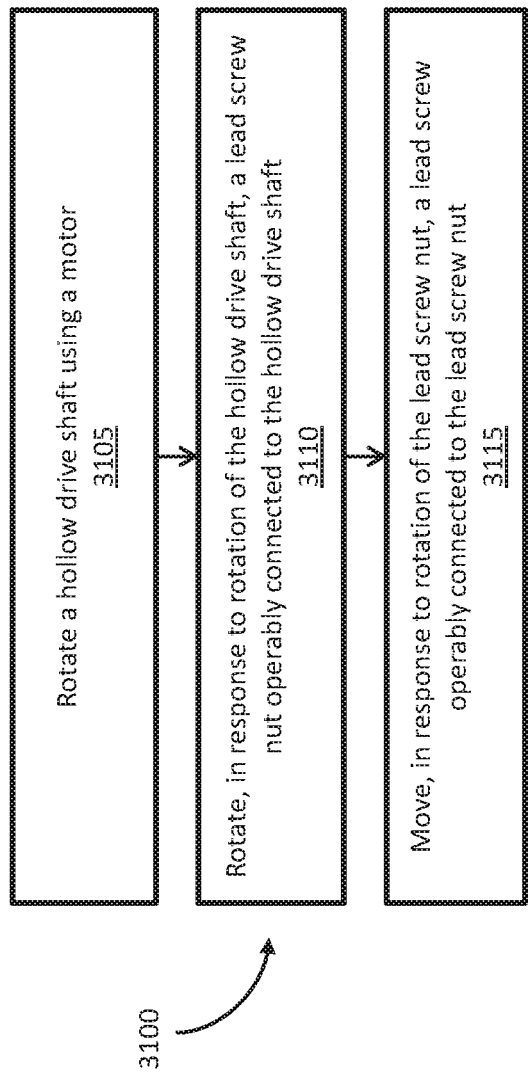

SYSTEMS AND METHODS FOR AUTOMATICALLY REMOVING A NEEDLE CAP OF AN AUTOINJECTOR

PRIORITY CLAIM

This application is a 371 U.S. National Stage application of International Application No. PCT/US2019/024086 filed Mar. 26, 2019, which claims priority to U.S. Provisional Application Nos. 62/648,762 filed Mar. 27, 2018, 62/648,766 filed Mar. 27, 2018, 62/648,770 filed Mar. 27, 2018 and 62/648,772 filed Mar. 27, 2018, their entire contents are incorporated herein by reference and relied upon.

TECHNICAL FIELD

The present disclosure relates to drug delivery with an injector device. In particular, several embodiments are directed to motor-driven delivery of medicaments with an electronic autoinjector device with a linear actuator.

BACKGROUND

Patients suffering from many chronic conditions must frequently inject themselves with medicament. A variety of drug delivery devices known as autoinjectors have been developed to enable a person to conveniently and reliably self-inject medicament. These devices utilize a liquid medicament for injecting into the person. Forward movement of a plunger results in the medicament being dispensed from an outlet opposite of the plunger.

Electronic autoinjectors have several advantages over purely mechanical autoinjectors, including clear user feedback, multiple delivery speeds and constant delivery force. However, for economic reasons, electronic autoinjectors are typically reusable, requiring the user to perform extra loading steps of a disposable syringe or dose cassette. Many electronic autoinjectors also use the motor drive mechanism to insert the needle into the user's tissue, resulting in a slower insertion process that can result in the perception of more pain.

SUMMARY

It is an object of the present disclosure to provide an electronic autoinjector device that reduces the number of manual steps, including rapid needle insertion for lower pain perception.

A device includes a motor having a hollow drive shaft. The motor is configured to rotate the hollow drive shaft. A lead screw nut is operably connected to the hollow drive shaft. The lead screw nut is configured to rotate upon rotation of the hollow drive shaft. A lead screw is operably connected to the lead screw nut. The lead screw is configured to move within the lead screw nut and the lead screw is configured to pass through at least part of the hollow drive shaft.

A method includes rotating, by a motor, a hollow drive shaft. The method further includes rotating, in response to rotation of the hollow drive shaft, a lead screw nut operably connected to the hollow drive shaft. The method further includes moving, in response to rotation of the lead screw nut, a lead screw operably connected to the lead screw nut. The lead screw is configured to pass through at least part of the hollow drive shaft.

An autoinjector device includes a controller, a plunger drive unit, a motor controlled by the controller, and a hollow drive shaft. The motor is configured to rotate the hollow drive shaft. The autoinjector device further includes a gear box operably connected to the hollow drive shaft and a lead screw nut operably connected to the gear box. The lead screw nut is configured to rotate in response to a rotational force from the hollow drive shaft exerted on the lead screw nut via the gear box. The autoinjector device further includes a lead screw operably connected to the lead screw nut. The lead screw is configured to move within the lead screw nut and is configured to pass through at least part of the hollow drive shaft. Movement of the lead screw in response to rotation of the lead screw nut is configured to cause a plunger head driver at a distal end of the lead screw to engage the plunger drive unit upon to dispense a medicament.

An autoinjector device includes a dose cassette. The dose cassette includes an outer container and a needle cap having a base with a diameter larger than the outer container. The autoinjector device further includes a housing configured to receive the dose cassette and a clasp mechanism configured to secure the dose cassette within the housing. The autoinjector device further includes an actuator configured to move the dose cassette proximally within the housing after the dose cassette is secured within the housing. The movement of the dose cassette causes the base of the needle cap to mechanically engage with a distal end of the housing. The mechanical engagement between the base of the needle cap and the distal end of the housing causes the needle cap to separate from the dose cassette.

A method includes receiving a dose cassette into a housing. The dose cassette includes an outer container and a needle cap having a base with a diameter larger than the outer container. The method further includes securing the dose cassette within the housing using a clasp mechanism. The method further includes moving the dose cassette proximally within the housing after the dose cassette is secured within the housing. The method further includes separating the needle cap from the dose cassette because of mechanical engagement between a distal end of the housing and the needle cap.

A dose cassette device includes an outer container and a needle cap having a base with a diameter larger than the outer container of the dose cassette. The outer container is configured to be inserted into a housing of an autoinjector. The base of the needle cap is configured to mechanically engage with a distal end of the housing. The needle cap is configured to separate from the outer container because of the mechanical engagement between the distal end of the housing and the base of the needle cap.

An autoinjector housing device includes a housing configured to receive a dose cassette having an outer container and a needle cap. The needle cap includes a base with a diameter larger than the outer container of the dose cassette. The autoinjector housing device further includes a clasp mechanism configured to secure the dose cassette within the housing. The autoinjector housing device further includes an actuator configured to move the dose cassette proximally within the housing after the dose cassette is secured within the housing. The movement of the dose cassette causes the base of the needle cap to mechanically engage with a distal end of the housing. The mechanical engagement between the base of the needle cap and the distal end of the housing causes the needle cap to separate from the dose cassette.

An autoinjector housing device includes a housing configured to receive a dose cassette and a base latch configured to secure the dose cassette within the housing. The autoinjector housing device further includes a back plate operably connected to a spring. The back plate is configured to move proximally within the housing upon receipt of the dose cassette into the housing. The proximal movement of the back plate compresses the spring. The autoinjector housing device further includes an actuator operably connected to the base latch. The actuator is configured to move the base latch and the dose cassette proximally within the housing after the dose cassette is secured in the housing. The base latch is configured to move radially outwards upon said proximal movement of the base latch within the housing. The radial movement of the base latch is configured to cause the dose cassette to become unsecured within the housing. In response to the dose cassette becoming unsecured, the spring is configured to decompress. The decompression of the spring is configured to move the back plate distally and push the dose cassette out of a distal end of the housing.

A method includes receiving a dose cassette at a housing of an autoinjector device. The method further includes securing the dose cassette within the housing using a base latch. The method further includes moving a black plate operably connected to a spring. The back plate moves proximally within the housing upon receipt of the dose cassette into the housing. The method further includes compressing the spring as a result of the proximal movement of the back plate within the housing. The method further includes moving, by an actuator operably connected to the base latch, the dose cassette and the base latch proximally within the housing after the dose cassette is secured in the housing. The method further includes ejecting the dose cassette from the housing in response to the proximal movement of the base latch and the dose cassette. The ejection of the dose cassette includes moving the base latch radially outwards upon said proximal movement of the base latch within the housing. The movement of the base latch causes the dose cassette to become unsecured within the housing. The ejection of the dose cassette further includes decompressing the spring in response to the dose cassette becoming unsecured. The ejection of the dose cassette further includes moving the back plate distally within the housing as a result of the decompression of the spring. The movement of the back plate pushes the dose cassette out of a distal end of the housing.

An autoinjector device includes a needle, a housing, and a primary container operably connected to the needle. The primary container is configured to move axially within the housing. The autoinjector device further includes a ledge fixed with respect to the housing and a first spring. A first end of the first spring is operably connected to the primary container and a second end of the first spring is operably connected to the housing. The autoinjector device further includes a latching mechanism operably connected to the primary container. The autoinjector device further includes a second spring. A first end of the second spring is operably connected to the latching mechanism and a second end of the second spring is operably connected to the primary container. The autoinjector device further includes a linear actuator configured to move axially within the housing. In a first state, the latching mechanism is biased toward the ledge by the second spring and the primary container and the needle are fixed within the housing based on mechanical engagement between the latching mechanism and the ledge. In a second state, the linear actuator engages and moves the latching mechanism such that the latching mechanism no longer mechanically engage with the ledge and the primary container and the needle, in response to the movement of the latching mechanism, move distally with respect to the housing based on an energy stored in the first spring.

A method includes moving a linear actuator axially within a housing to engage the linear actuator with a latching mechanism operably connected to a primary container. The primary container is operably connected to a needle and is configured to move axially within the housing. A first spring has a first end operably connected to the primary container and a second end operably connected to the housing. The latching mechanism is operably connected to the primary container and is biased toward a ledge by a second spring. The ledge is fixed with respect to the housing. The second spring has a first end operably connected to the latching mechanism and a second end operably connected to the primary container. The primary container and the needle are fixed within the housing based on mechanical engagement between the latching mechanism and the ledge before the linear actuator is engaged with the latching mechanism. The method further includes moving, in response to engagement of the linear actuator with the latching mechanism, the latching mechanism such that the latching mechanism no longer mechanically engages with the ledge. The method further includes moving, in response to the movement of the latching mechanism, the primary container and the needle distally with respect to the housing based on an energy stored in the first spring.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. For ease of reference, throughout this disclosure identical reference numbers may be used to identify identical or at least generally similar or analogous components or features.

FIG. 13 is a sectioned perspective view of a portion of a dose cassette in accordance with the disclosed embodiments.

FIG. 15 is a sectioned perspective view of a reusable autoinjector base and a dose cassette just prior to the dose cassette being inserted into the reusable autoinjector base in accordance with the disclosed embodiments.

FIG. 16 is a sectioned perspective view during an insertion of a dose cassette into a reusable autoinjector base in accordance with the disclosed embodiments.

FIG. 17 is a sectioned perspective view of a dose cassette locked into a reusable autoinjector base in accordance with the disclosed embodiments.

FIG. 21 is a sectioned perspective view of a needle cap of a dose cassette contacting a sensor of a reusable autoinjector base in accordance with the disclosed embodiments.

FIG. 22 is a sectioned perspective view of a needle cap of a dose cassette being removed in accordance with the disclosed embodiments.

FIG. 24 is a sectioned perspective view of a dose cassette locked in place in advance of a needle protruding from the dose cassette in accordance with the disclosed embodiments.

FIG. 25 is a sectioned perspective view of a needle protruding from a dose cassette in accordance with the disclosed embodiments.

FIG. 29 is a sectioned perspective view of a dose cassette being ejected from a reusable autoinjector base in accordance with the disclosed embodiments.

FIG. 30 is a sectioned perspective view of an ejected dose cassette in accordance with the disclosed embodiments.

FIG. 31 is a flow diagram illustrating a method for utilizing a linear actuator with a hollow drive shaft in accordance with the disclosed embodiments.

DETAILED DESCRIPTION

Figure 1:
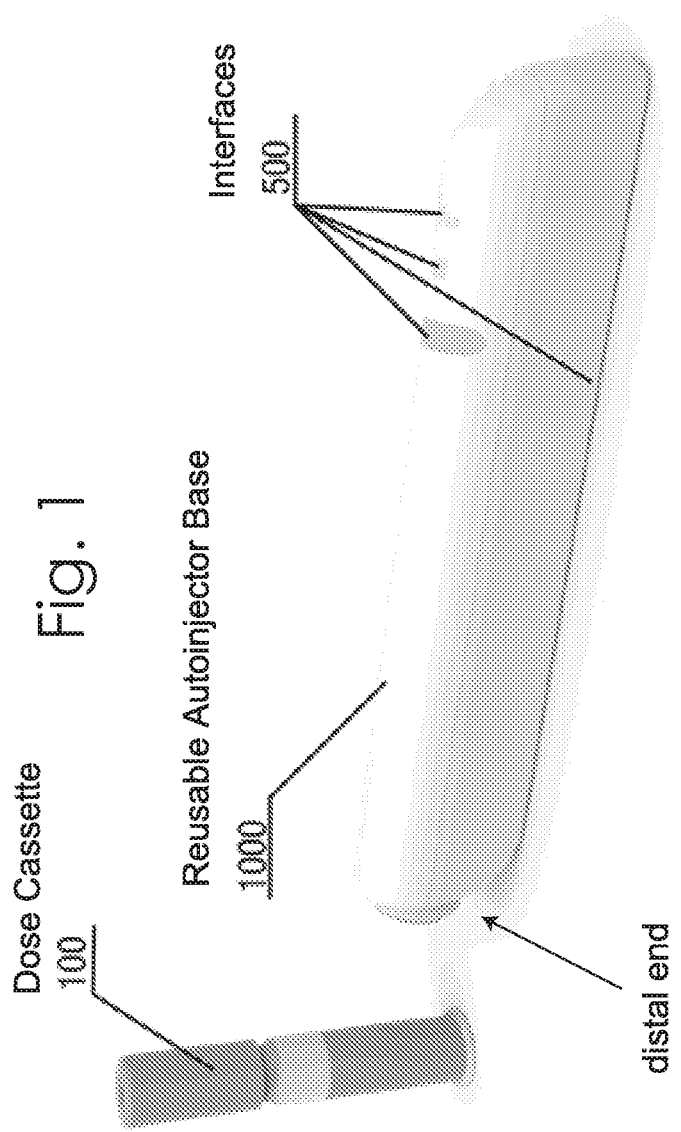
FIG. 1 is a perspective view of a reusable autoinjector base and a dose cassette in accordance with the disclosed embodiments.

The present technology is directed to apparatuses, systems, methods, and computer readable media for a medical autoinjector. In some embodiments, the autoinjector includes a reusable autoinjector base and disposable dose cassettes, which may be disposed of after one or more uses. The dose cassettes can be inserted into the autoinjector, which in turn automatically dispenses a medicament and records that the medicament was dispensed. In some embodiments, the autoinjector may be reusable. In some embodiments, instead of having a separate disposable dose cassette, the entire autoinjector may be disposable after one or more uses. In some embodiments, the autoinjector may be used repeatedly during for a predetermined amount of time.

Advantageously the embodiments described herein include a single-motor driven mechanism that automates processes for removing a needle cap, rapidly inserting a needle to patients, delivering drug/medicament, retracting the needle, and/or ejecting a dose cassette.

As described herein, an autoinjector includes a linear actuator having an electric motor. The electric motor has a hollow drive shaft, which allows a lead screw to pass through the center of the motor. Thus, the hollow drive shaft enables the autoinjector to have a smaller overall footprint compared to implementations where a motor is adjacent to a lead screw and the lead screw is connected to the motor via an output shaft and a gearbox. For handheld medical devices such as autoinjectors, a small footprint is desirable, especially so that such devices can have compact, cylindrical footprints. In some embodiments, additional stages may be added concentrically to a gearbox that has a hollow center. The hollow center of the gearbox may be aligned with the hollow drive shaft of the motor. Thus, such a configuration of the gearbox can significantly increase the torque output without significantly adversely affecting the overall footprint of the autoinjector.

Also described herein are embodiments for automated needle cap removal of an autoinjector. Automated needle cap removal has several benefits. First, automating removal of a needle cap ensures that the needle cap is properly removed to lower the chance of: a device malfunction, patient injury, and improperly delivered medicament. Such features may be especially beneficial for users with physical or mental challenges that make handling an injection device and/or following multiple steps for using an injection device difficult. The automated needle cap removal described herein may ensure (e.g., using sensors) that a needle cap was properly removed before proceeding with an injection process.

Also described herein are embodiments for automated rapid needle insertion of an injection device. In various embodiments, the insertion of a needle into a user's skin is automated and not in direct response to a button press or other action performed by the user. In other words, in various embodiments, an injection device first determines whether conditions are proper for an injection (e.g., dose cassette properly inserted, device properly placed on skin, needle cap properly removed, etc.) and then automatically initiates the injection (i.e., insertion of a needle) after determining that the conditions are proper without a particular button press or other action performed by the user. This can help abstract the injection process away from the user, reducing anxiety that may be associated with needles and injections for some users. The various embodiments of automated needle insertion described herein also provide for mechanisms that ensure a needle is inserted to the correct depth so that medicament is properly delivered. With a manual insertion, needle insertion depth may not always be ideal. The needle insertion described herein also occurs rapidly (e.g., through a spring-driven insertion) compared to a manual insertion process, reducing the amount of time the tissue is being disrupted by a needle and thereby improving the overall comfort for the user during the injection process. The rapid needle insertion embodiments disclosed herein may be used with any type of autoinjection device, whether the device uses disposable dose cassettes or not.

Various embodiments disclosed herein also provide for automated dose cassette ejection for autoinjectors that utilize a reusable autoinjector base and disposable dose cassettes. Automatically removing a used dose cassette after completion of an injection reduces the amount time a user needs to handle the dose cassette that has a needle and ensures that dose cassette is removed properly, thereby reducing the possibility of injury to the user and/or damage to a reusable autoinjector base. This advantageously simplifies the steps that a user needs to perform, which may be particularly beneficial for any user with physical or mental challenges that affect usage of an injection device.

Specific details of several embodiments of the technology are described below with reference to FIGS. 1-36. Although many of the embodiments are described below with respect to devices, systems, methods, and computer readable media for improved autoinjectors, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-36.

Overview

FIG. 1 is a perspective view of a reusable autoinjector base 1000 and a dose cassette 100 in accordance with the disclosed embodiments. Dose cassettes may also be referred to herein as a pod. The reusable autoinjector base 1000 includes interfaces 500. Interfaces 500 may include, for example, LEDs (light emitting diodes), buttons, screens, and/or other types of user interfaces for communicating a state of the autoinjector, dose cassette, medicament, or other aspect to the user or to receive inputs from the user. The dose cassette 100 is sized to fit within an opening (not shown) in the reusable autoinjector base 1000, but exists on a distal end (the left end in FIG. 1) of a housing of the reusable autoinjector base 1000. Once the dose cassette 100 is inserted in the reusable autoinjector base 1000, a medicament stored in the dose cassette 100 can be delivered as described below.

Figure 2:
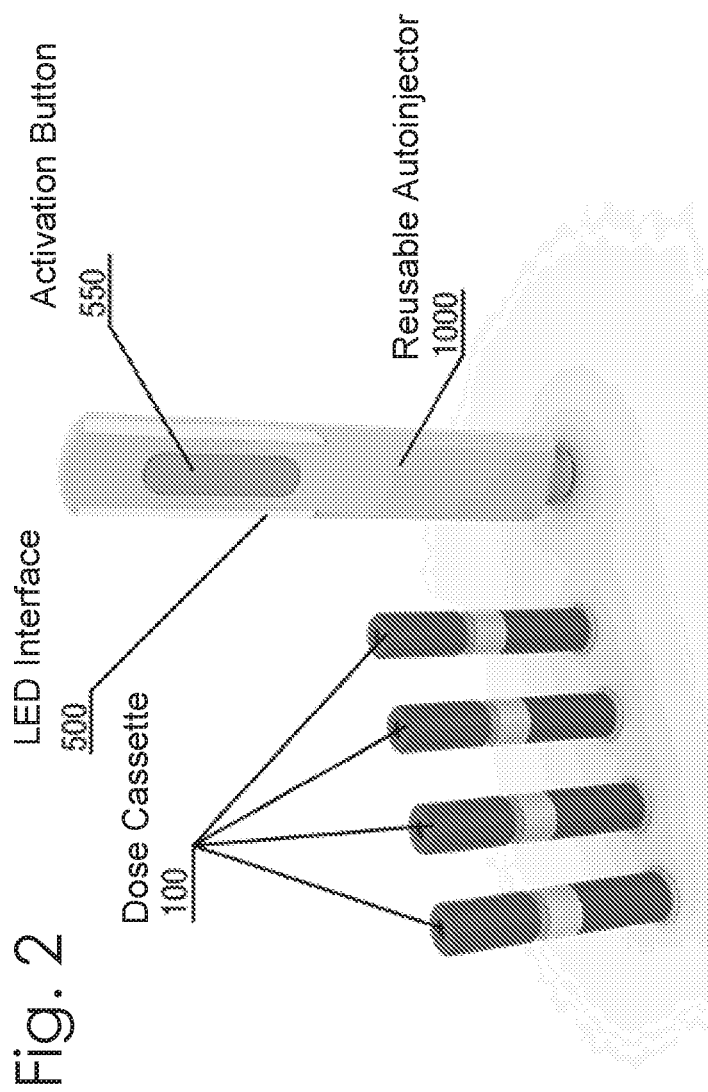
FIG. 2 is a perspective view of another reusable autoinjector base and multiple dose cassettes in accordance with the disclosed embodiments.
Figure 3:
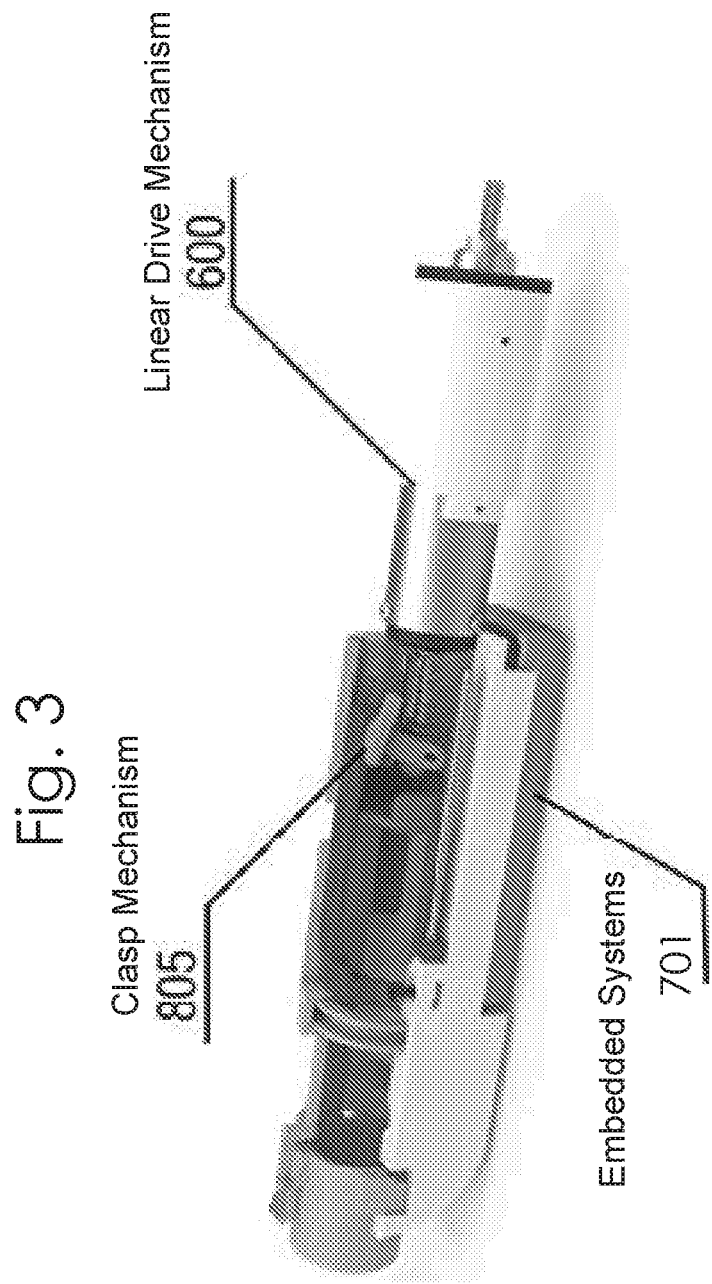
FIG. 3 is a sectioned perspective view of a reusable autoinjector base in accordance with the disclosed embodiments.

FIGS. 2 and 3 are discussed together below, as they each show different views of a reusable autoinjector base 1000 and/or dose cassettes 100. FIG. 2 is a perspective view of a reusable autoinjector base 1000 and multiple dose cassettes 100 in accordance with the disclosed embodiments. FIG. 3 is a sectioned perspective view of the reusable autoinjector base 1000 in accordance with the disclosed embodiments.

As shown in FIGS. 2-3, the reusable autoinjector base 1000 includes, among other things, an LED interface 500, an activation button 550, a linear drive mechanism including a linear actuator 600, embedded systems 701, a clasp mechanism 805. Once a dose cassette is successfully inserted into the reusable autoinjector base 1000, the activation button 550 may be pressed to initiate needle cap removal, injection, needle withdrawal, and/or dose cassette ejection.

The LED interface 500 may indicate various information such as whether an injection was successful and/or whether the dose cassette was successfully inserted in the reusable autoinjector base 100. As further described below, the dose cassettes 100 is sized to fit into the reusable autoinjector base 1000, such that medicament stored in the dose cassettes 100 can be dispensed into a user.

The linear drive mechanism may arranged to drive a plunger (e.g., of a syringe), thereby causing dispensation of the medicament in the secondary container (e.g., the dose cassette 100). The linear drive mechanism may be further arranged to actuate the needle insertion and retraction mechanism within the dose cassettes 100 and to actuate a dose cassette 100 release/ejection mechanism.

The clasp mechanism 805, as will be described in greater detail below, locks/secures the dose cassette 100 within the reusable autoinjector base 1000 and releases the dose cassette 100 after the injection is complete and the needle is retracted back into the dose cassette.

The embedded systems 701 may include a printed circuit board (PCB) having various integrated circuits and passive components, a radio frequency transmitter to transmit data, and/or a battery. The embedded systems 701 may be configured to receive signals from, for example, a radio frequency identification (RFID) reader. The embedded systems 701 may also be configured to send control signals to the linear drive mechanism.

Linear Actuators

Figure 4:
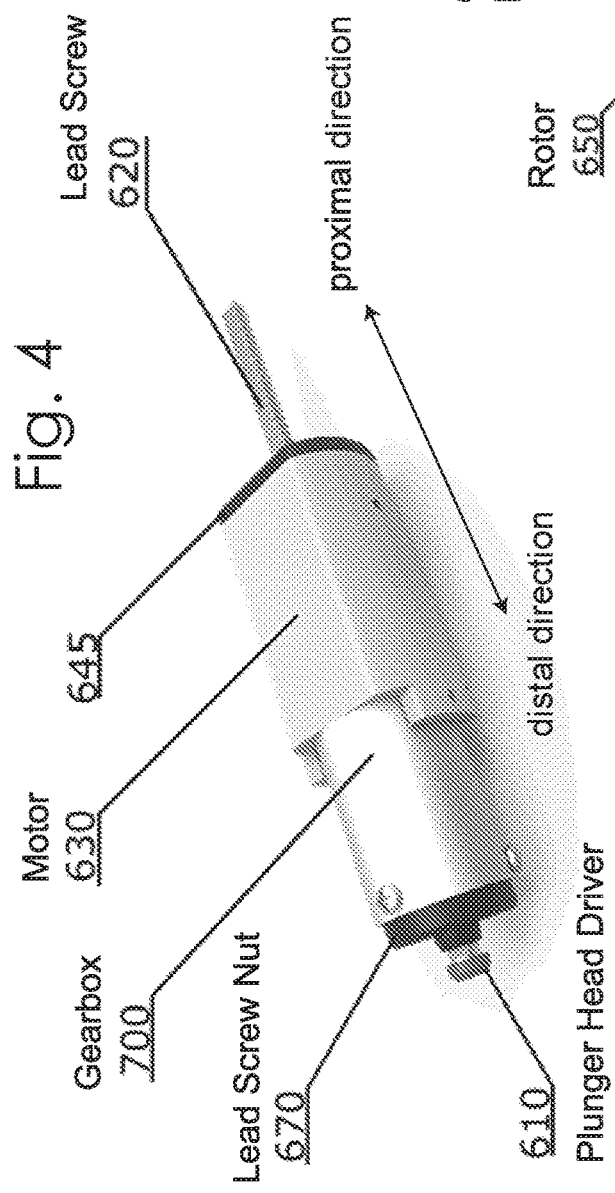
FIG. 4 is a perspective view of a linear actuator with a hollow drive shaft and a gear box in accordance with the disclosed embodiments.
Figure 5:
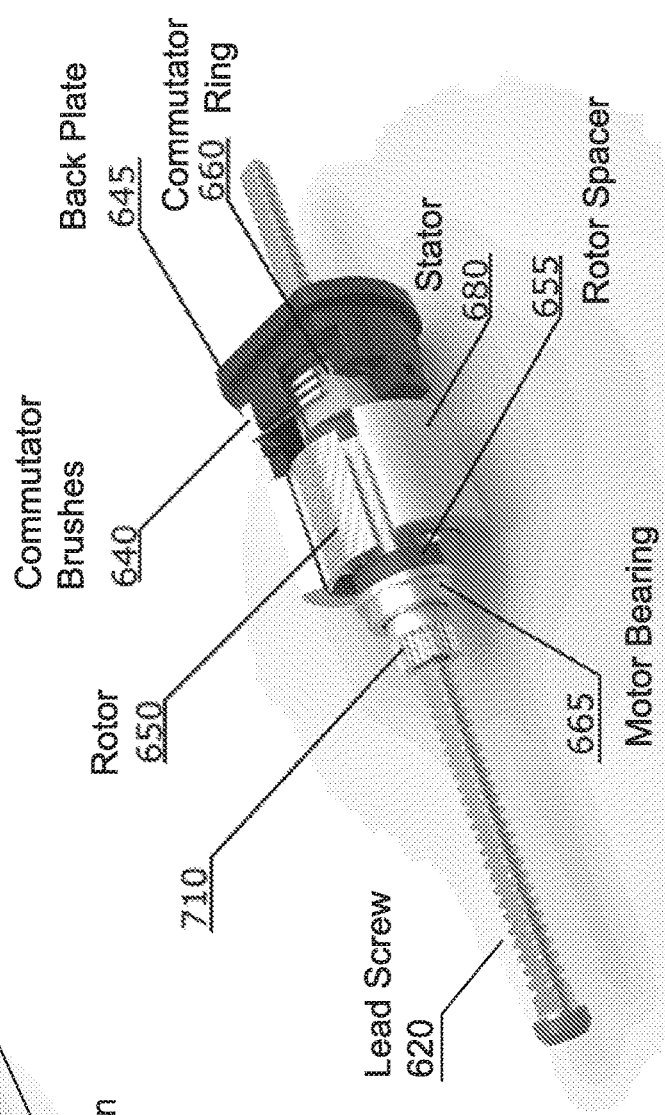
FIG. 5 is a sectioned perspective view of a motor with a hollow drive shaft and a lead screw in accordance with the disclosed embodiments.
Figure 6:
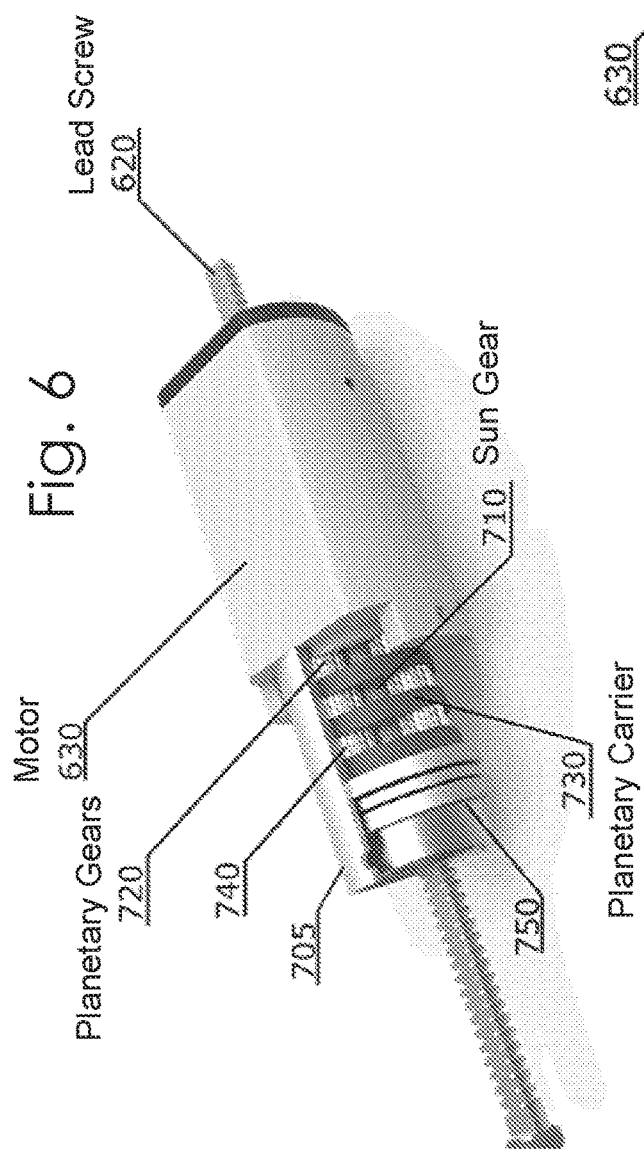
FIG. 6 is a sectioned perspective view of a linear actuator and a gear box in accordance with the disclosed embodiments.
Figure 7:
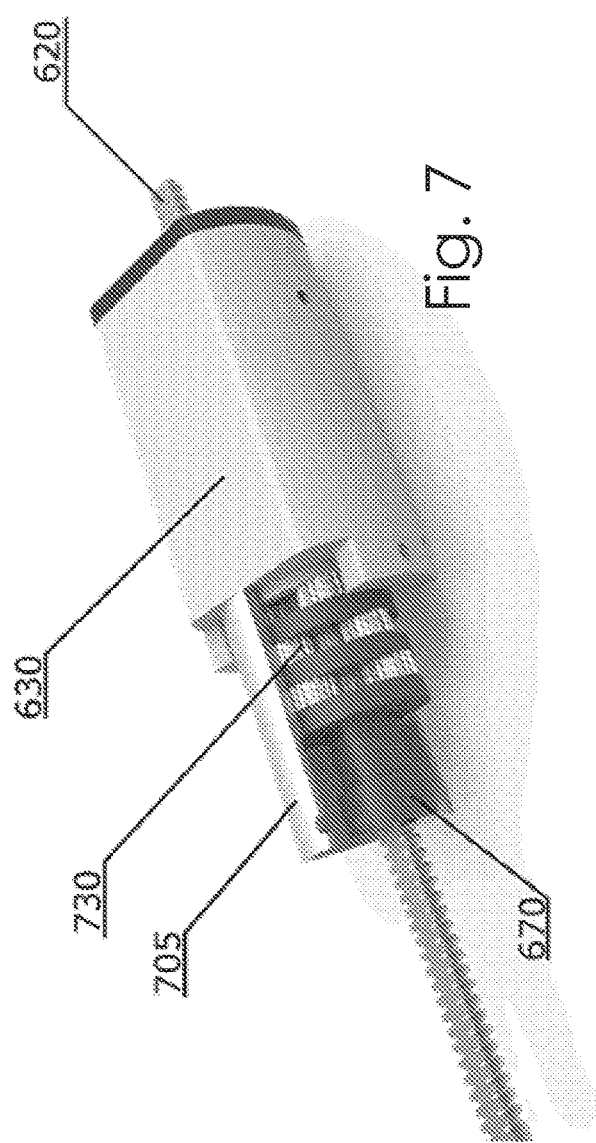
FIG. 7 is another sectioned perspective view of a linear actuator and a gear box in accordance with the disclosed embodiments.
Figure 8:
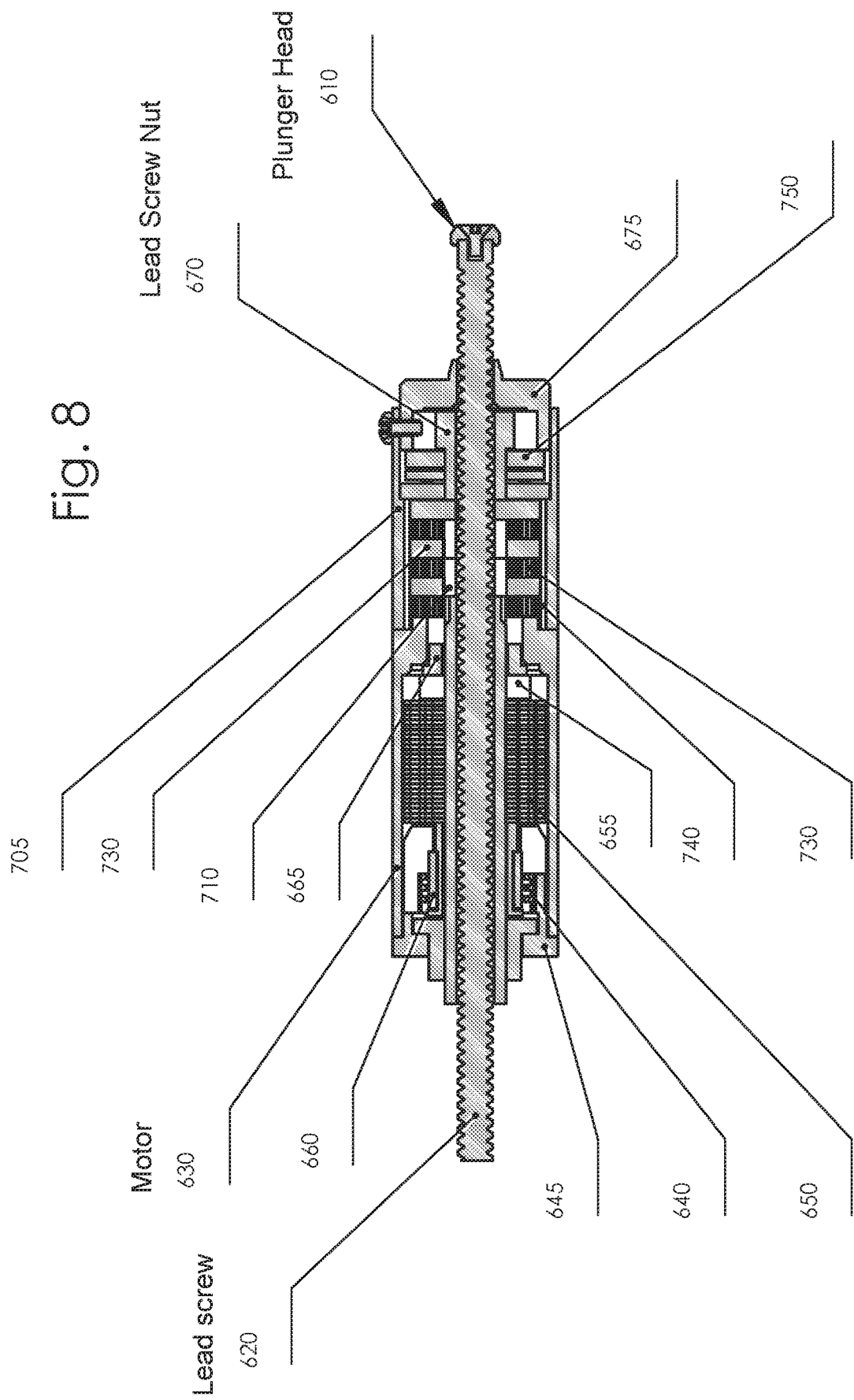
FIG. 8 is a cross-section view of a linear actuator and a gear box in accordance with the disclosed embodiments.

FIGS. 4-8 are discussed together below, as they each show different views of a linear actuator as described herein. FIG. 4 is a perspective view of a linear actuator 600 including a motor 630 having hollow drive shaft and a gear box 700 in accordance with the disclosed embodiments the disclosed embodiments. FIG. 5 is a sectioned perspective view of a motor 630 having a hollow drive shaft and a lead screw 620 in accordance with the disclosed embodiments. FIG. 6 is a sectioned perspective view of a linear actuator 600 and a gear box 700 in accordance with the disclosed embodiments. FIG. 7 is another sectioned perspective view of a linear actuator 600 and a gear box 700 the disclosed embodiments in accordance with the disclosed embodiments. FIG. 8 is a cross-section view of a linear actuator 600 and a gear box 700 in accordance with the disclosed embodiments.

As discussed above, the linear actuator 600 may be utilized in an autoinjector (e.g., in the reusable autoinjector base 1000 described herein). As shown in FIGS. 4-8, the linear actuator 600 includes the motor 630, the gearbox 700, the lead screw 620, and a plunger head driver 610. The motor 630 is of a brushed DC motor design that has a hollow drive shaft to allow the lead screw 620 to move through the middle of the motor 630. Although a brushed DC motor is shown in FIGS. 4-8, other types of motors may also be utilized. The lead screw 620 can move proximally and distally with respect to a plane of lead screw 620's rotation via a lead screw nut 670. The lead screw nut 670 is attached to the gearbox 700, which in turn is attached to the hollow drive shaft of the motor 630. Accordingly, as the hollow drive shaft is turned (e.g., when motor 630 is powered), the lead screw nut 670 is also turned/rotated via gears in gearbox 700. Depending on the direction of rotation of the hollow drive shaft, the lead screw 620 can may move proximally or distally through the hollow center of the motor 630. Thus, the plunger head driver 610, which is fixed to the lead screw 620, moves with the lead screw 620 proximally or distally to engage the various aspects of an autoinjector to implement the various features of the disclosed autoinjector (e.g., removing a needle cap, rapidly inserting a needle to patients, delivering drug/medicament, retracting the needle, and/or ejecting a dose cassette). In addition, the gearbox 700 may also have a hollow center that is aligned with the hollow center of the motor 630 such that that the lead screw 620 can move proximally or distally through both the center of the motor 630 and the center of the gearbox 700.

As utilized herein, when two aspects of the disclosure are operably connected, the two aspects may or may not be directly connected unless otherwise specified. For example, the lead screw nut 670 and the hollow drive shaft may or may not be directly connected. In the examples of FIGS. 4-8, the lead screw nut 670 and the hollow drive shaft are operably connected through the gearbox 700 because rotation of the hollow drive shaft by the motor 630 also causes the lead screw nut 670 to rotate via the gearbox 700. As discussed, this rotation engages the lead screw 620 such that the lead screw 620 moves proximally or distally within an autoinjector and within the hollow centers of the gearbox 700 and/or the hollow drive shaft of the motor 630. Accordingly, two aspects of the various embodiments described herein as operably connected may be directly connected or may be connected by an intermediate aspect of the embodiments discussed herein.

In one instance, the lead screw nut 670 rotates in a direction that causes the lead screw 620, and thus the plunger head driver 610, to move in a proximal direction toward the gearbox 700 and the motor 630. It is desirable to cause the plunger head driver 610 not to move into the lead screw nut 670 however. Accordingly, the lead screw 620 can have flat surfaces at a distal end of the lead screw 620, just before the plunger head driver 610 at the distal-most end of the lead screw 620. In addition, the distal-most end of the gearbox 700 has at least two flat surfaces that can contact the at least two flat surfaces of the lead screw 620. Thus, if the lead screw 620 moves far enough in a proximal direction, the flat surfaces of the gearbox 700 contact the flat surfaces of the lead screw 620 preventing further rotational motion of the lead screw 620 (at least in a direction that would cause the lead screw 620 to move further in the proximal direction). This keeps the plunger head driver 610 from entering inside the lead screw nut 670, and also ensures that the lead screw nut 670 stays engaged with the lead screw 620. In various embodiments, similar surfaces may also be implemented at a proximal end of the lead screw 620 and motor 630 to prevent the lead screw from moving past the proximal end of the motor 630. In other embodiments, such similar surfaces may be implemented somewhere between the proximal end of the motor 630 and the distal-most end 675 of the gearbox 700, to prevent an end of the lead screw 620 from reaching the lead screw nut 670 and potentially causing the lead screw and the lead screw nut 670 from coming disengaged. Other methods for preventing the lead screw 620 from moving further than desired may also be utilized. For example, a position of the lead screw 620 and/or the plunger head driver 610 may be tracked. This information can be utilized to ensure that signals sent to the motor never cause the lead screw 620 to move farther than desired in one or more direction.

In some embodiments, the lead screw 620 may further include surfaces that engage with surfaces of a gearbox 700 or surfaces of other components to prevent the lead screw 620 from rotating. By preventing rotation of lead screw 620, but still allowing it to move axially, the rotational torque of the lead screw nut 670 and/or one or more gears of gearbox 700 is translated into linear force exerted by the lead screw 620. In these embodiment, the surfaces of lead screw 620 and/or surfaces of a gearbox 700 or surfaces of other components may be in any shape. In some embodiments, the lead screw 620 and gearbox 700/other components may each include one surface for preventing the lead screw 620 from moving in a first direction. In some embodiments, the lead screw 620 and gear box 700/other components may each include another surface for preventing the lead screw 620 from moving in a second direction opposite to the first direction.

Referring now to FIG. 5, the motor 630 includes a rotor 650 and coil windings. The coils get energized through the motor base via a commutator ring 660 through commutator brushes 640, and held in place by the back plate 645. The motor rotor 650 is held in place with a rotor spacer 655 and motor bearings 665. A stator 680 includes two or more solid-state magnets. In various embodiments, other types of motors than the one shown in FIG. 5 may be utilized with the autoinjectors discussed herein.

Referring now to FIGS. 5-7, the gearbox 700 includes a planetary gear set comprising at least one stage of a sun gear 710, planetary gears 720, a planetary carrier 730, and a ring gear 740. For multiple stages, the planetary carrier 730 is rigidly attached to the next stage sun gear 710. The forward-most planetary carrier 730 is rigidly attached to the lead screw nut 670. The ring gear 740 may be hobbed into the gearbox housing 705. The lead screw nut 670 exerts force on one or more bearings 750 providing linear and radial rigidity. In various embodiments, other configurations of gearboxes may be utilized with the various autoinjectors discussed herein. In some embodiments, no gearbox may utilized, and a drive shaft of the motor 630 may be connected directly to the lead screw nut 670. In some embodiments, the drive shaft of the motor 630 may include the lead screw nut 670.

FIG. 8 shows a cross section of a linear actuator 600 and with regards to FIGS. 4-7 above. As can be seen in FIG. 8, the lead screw 620 passes through a hollow drive shaft of the motor 630 and a hollow center of the gearbox 700. Advantageously, this allows for a small cylindrical package that can fit well into an autoinjector, and the linear actuator can be utilized to implement several different functions of the autoinjectors as described herein.

Needle Cap Removal

Figure 9:
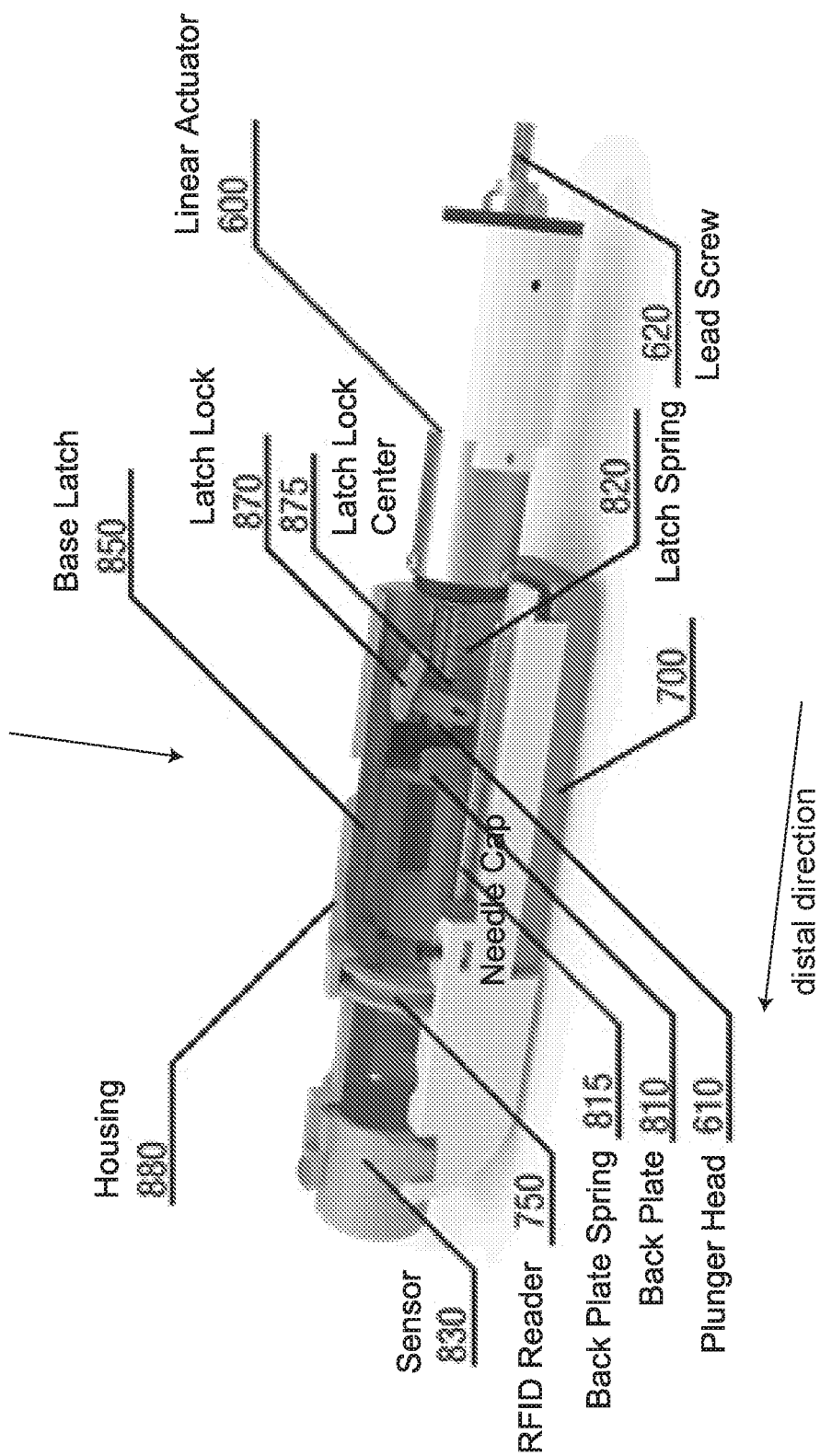
FIG. 9 is a sectioned perspective view of a reusable autoinjector base in accordance with the disclosed embodiments.

FIG. 9 is a sectioned perspective view of a reusable autoinjector base in accordance with the disclosed embodiments the disclosed embodiments. The reusable autoinjector base shown in FIG. 9 includes a clasp mechanism 805, a backplate 810, a sensor 830, and a housing 880. Also shown in FIG. 9 are embedded systems 701, a linear drive mechanism 600, a lead screw 620, and a plunger head driver 610. The linear drive mechanism 600 includes a motor with a hollow drive shaft. For example, the linear drive mechanism 600 may be the drive mechanism described above with respect to FIGS. 4-8 above. The pod clasp mechanism 805 includes a latch lock 870, a latch lock center 875, a latch lock spring 820, and a base latch 850, the functions of each of which will be disclosed in more detail below.

In the distal-most position of the clasp mechanism 805, the latch lock spring 820 is decompressed, rotating the latch lock 870, and locking the pod clasp mechanism to the housing 880. This prevents the clasp mechanism 805 from moving axially within the housing. When the latch lock 870 is rotated, the clasp mechanism 805 becomes unlocked from the housing 880, allowing for axial movement of the clasp mechanism 805 within the housing 880. This feature is described in more detail herein, for example with respect to FIGS. 19 and 20 below.

Figure 11:
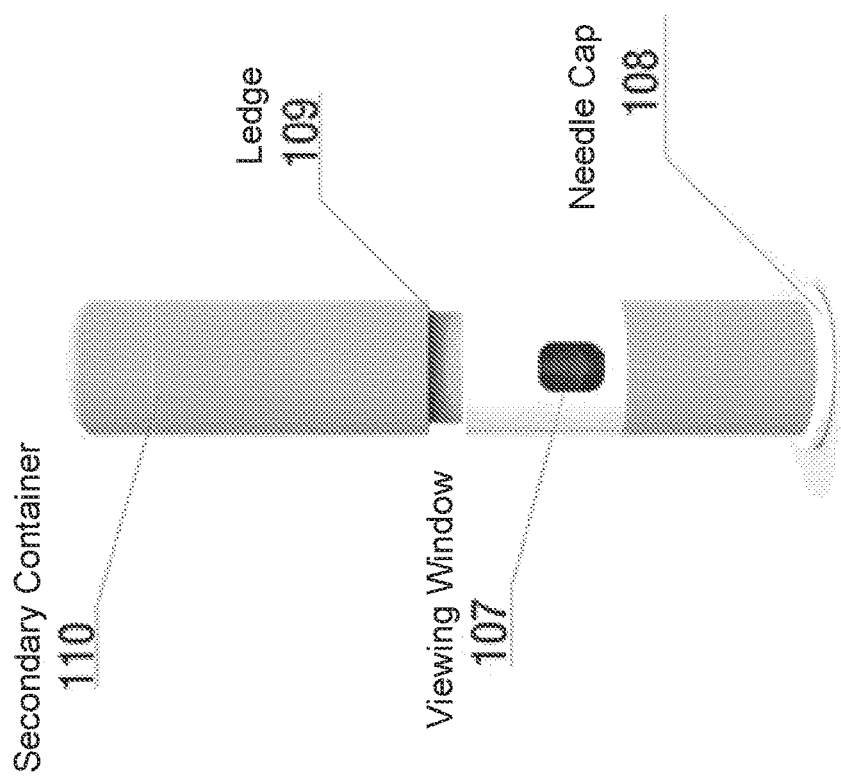
FIG. 11 is a perspective view of a dose cassette in accordance with the disclosed embodiments.

Upon insertion of a dose cassette into the autoinjector base, the base latch 850 is pushed radially outwards (shown, e.g., in greater detail in FIG. 16), allowing the dose cassette to pass the base latch 850, and fix to a ledge of a dose cassette (e.g., ledge 109 shown in FIG. 11). In addition, the backplate 810, which is biased distally via a backplate spring 815, is pushed back by the dose cassette being inserted, compressing the backplate spring 815 (e.g., as shown in FIG. 17). When the dose cassette is in the locked position, an RFID reader 750 can reads data from a dose cassette RFID tag (e.g., the RFID tag 104 in FIG. 12). This data may include information such as information about medicament stored in a dose cassette, a date of manufacture of the medicament and/or the dose cassette, a unique identifier of the dose cassette used to track the dose cassette, a dosage amount in the dose cassette, and/or any other information.

Once the dose cassette is latched and fixed into the autoinjector base, the linear drive mechanism 600 moves the lead screw 620 and plunger head driver 610 proximally (i.e., the plunger head driver 610 is moved toward the motor 630). The plunger head driver 610 engages with the latch lock center 875, moving the latch lock center 875 and the plunger head driver 610 in unison in a proximal direction (i.e., toward the motor 630). The latch lock center 875 is attached to the latch lock 870, so the motion of the latch lock center 875 rotates the latch lock 870, disengaging the clasp mechanism 805 from the housing 880, allowing the clasp mechanism 805 to move proximally within the housing 880. This process is described in further detail below with respect to FIGS. 15-20 below.

Once the latch lock 870 is unlocked, the entire clasp mechanism 805 can be moved proximally within the housing 880, including the base latch 850 that has locked in a dose cassette. Accordingly, the dose cassette will also move proximally within the housing 880 as the plunger head driver 810, the latch lock center 875, the latch lock 870, and the base latch 850 move proximally (i.e., toward the motor 630) within the housing 880. Accordingly, a rigid needle cap of the dose cassette can then mechanically engage with the sensor 830 while the rest of the dose cassette moves proximally along with the clasp mechanism 805, removing the needle cap. This process is described in further detail with respect FIGS. 19-23. In some embodiments, the needle cap may mechanically engage with a portion of the housing 880 instead of, or in addition to the sensor 830. In some embodiments, the sensor 830 is considered to be a part of the housing 880 or is incorporated into the housing 880, such that the mechanical engagement that removes the needle cap is between the needle cap and the housing 880.

After the needle cap of the dose cassette is removed, the lead screw 620 and plunger head driver 610 return to the previous position (which is similar to the position shown in FIG. 9). Thus, the latch lock spring 820 rotates the latch lock 870 back into a locked position, locking the clasp mechanism 805 into a position such that it cannot move axially within the housing 880. This process is discussed further with respect to FIGS. 21-24. The plunger head driver 610 can then move distally (i.e., away from the motor 630) to commence needle insertion, drug delivery, and needle retraction within a dose cassette as described herein including with respect to FIGS. 11-14 and 26.

Dose Cassette Removal

After needle insertion, drug delivery, and needle retraction, the plunger head driver 610 returns back to a position similar to that shown in FIG. 9. A dose cassette can then be ejected from the autoinjector base. To eject the dose cassette, the lead screw 620 and plunger head driver 610 move proximally (i.e., toward the motor 630 within the housing 880) along with the clasp mechanism 805 in a similar way as during the needle cap removal. However, for dose cassette ejection, the clasp mechanism 805 moves to a point beyond the previous position at which the needle cap was removed. This point may be a proximal-most position of the clasp mechanism 805 and plunger head driver 610. The base latch 850 then mechanically engages with the housing 880 via a ramp on the base latch 850, causing the base latch to move radially outwards and unlatch a dose cassette. In other words, the base latch 850 is removed from a ledge of a dose cassette. Once the base latch 850 is not securing a dose cassette, the tension in the backplate spring 815 decompresses, pushing the backplate 810 and a dose cassette distally, expelling the dose cassette from the autoinjector base through an opening at the distal end of the autoinjector base through which the dose cassette was originally inserted (e.g., at an end of the autoinjector base where the sensor 830 is located). The backplate 810 is not connected to any components of the clasp mechanism 805 (e.g., the base latch 850, the base latch lock 870, the latch lock center 875, and the latch lock spring 820). Accordingly, the backplate 810 can move independently of the clasp mechanism 805 to eject a dose cassette when the back plate spring 815 decompresses. By pulling the clasp mechanism 805 back to a proximal-most position as described above while the base latch 850 still secures a dose latch, the back plate spring can be compressed to store energy significant enough to eject the dose cassette complete from the autoinjector base once the base latch 850 no longer secures the dose cassette within the housing 880. This process is described herein further with respect to FIGS. 27-30. A user can check a dose cassette (e.g., viewing window 107 of FIG. 11) after it has been ejected to ensure the medicament in the dose cassette was expelled properly and/or in its entirety.

The lead screw 620 and plunger head driver 610 can then move distally, back to a previous position as shown in FIG. 9, locking the pod clasp mechanism 805 to the housing 880, which is a reset position of the autoinjector base. That is, the autoinjector base is now configured to receive a subsequent dose cassette and repeat the various processes described herein to inject a user and dispense a medicament.

Figure 10:
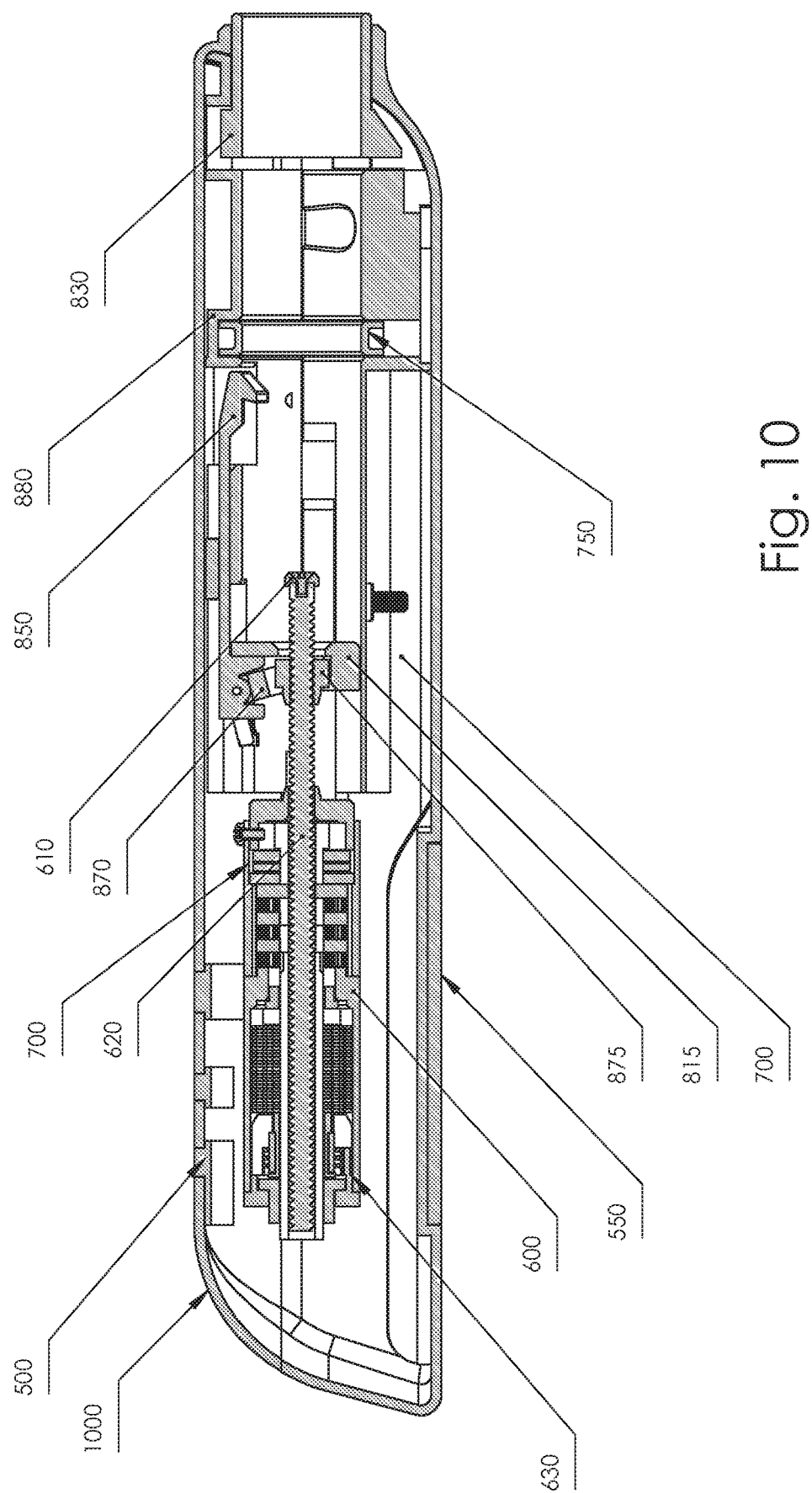
FIG. 10 is a cross-section view of a reusable autoinjector base in accordance with the disclosed embodiments.

FIG. 10 is a cross-section view of the reusable autoinjector base 1000 in accordance with the disclosed embodiments. In particular, FIG. 10 shows another view of the aspects of an autoinjector base as described above with respect to FIG. 9. It shows the reusable autoinjector base 1000 without a dose cassette. It also includes the linear actuator 600 as described herein having a hollow drive shaft and gearbox 700 with a hollow center that allows the lead screw 620 to pass through.

The lead screw 620 includes a plunger head driver 610 that has a diameter wider than an opening in the latch lock center 875. In this way, when the linear actuator 600 rotates the lead screw 620 to move the plunger head driver 610 proximally (i.e., toward the motor 630) within the housing 880 of the reusable autoinjector base 1000, the plunger head driver 610 mechanically engage with the opening of the latch lock center 875, such that the latch lock center 875 can be pulled in a proximal direction (i.e., toward the motor 630) by the plunger head driver 610. This proximal movement creates a force that overcomes a bias of the latch lock spring 820 to rotate the latch lock 870 as described herein, unlocking the latch lock 870 from the housing 880 and allowing the clasp mechanism 805 to move axially within the housing. Because the plunger head driver 610 can continue to mechanically engage with the latch lock center 875, which is part of the clasp mechanism 805, the plunger head driver 610 can move further in a proximal direction within the housing 880 to implement various functionalities described herein, including removal of a needle cap and ejecting a dose cassette. When the plunger head driver 610 is in a more distal position away from the latch lock center 875 as shown in FIG. 10, the plunger head driver 610 is not engaged with the latch lock center 875. In this way, the plunger head driver can move into a dose cassette to implement needle insertion, dose delivery, and needle retraction as described herein. Accordingly, the single linear actuator 600 with the lead screw 620 and the plunger head driver 610 can be advantageously utilized to implement each of locking of an inserted dose cassette, removal of a needle cap of the dose cassette, needle insertion into the user of a needle in the dose cassette, dosage delivery of a medicament stored in the dose cassette, retraction of the needle back into the dose cassette, and ejection of the spent dose cassette as described herein.

Needle Insertions/Retraction and Medication Administration

Figure 12:
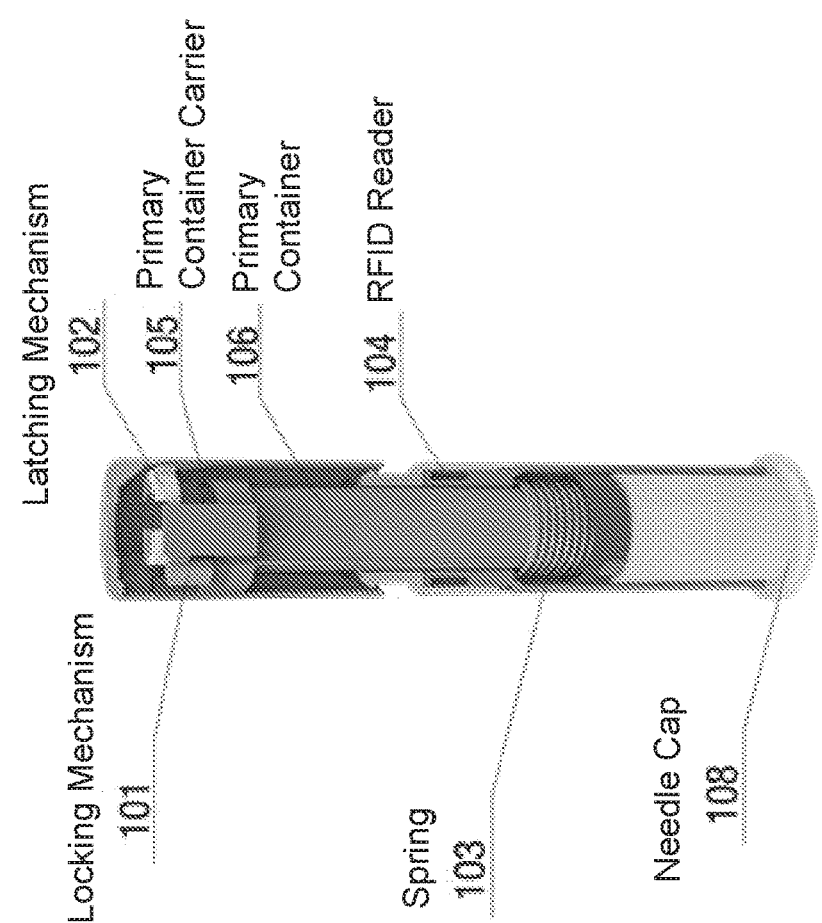
FIG. 12 is a sectioned perspective view of a dose cassette in accordance with the disclosed embodiments.

FIG. 11 is a perspective view of a dose cassette in accordance with the disclosed embodiments. FIG. 12 is a sectioned perspective view of a dose cassette in accordance with the disclosed embodiments. The dose cassette includes an outer secondary container 110, the primary container 105 filled with medicament, a primary container carrier 106, at least one spring 103 to bias the primary container, a needle cap 108, a locking mechanism 101 to fix the primary container 105 within the dose cassette prior to activation, a latching mechanism 102 to release the primary container from this fixed position via the linear actuator, a primary container viewing window 107, and an RFID tag 104 to store drug/medicament information. The dose cassette also includes a ledge 109 that allows the base latch of an autoinjector to lock the dose cassette in place. The primary container 105 may be biased distally by the spring 103. During transportation and storage, the dose cassette needle insertion and retraction latching mechanism 102 is locked due to the position of the needle cap 108, which secures the locking mechanism 101. The locking mechanism 101 is biased distally and mechanically engaged (or "interferes") with the latch mechanism 102 when the needle cap 108 is in place, such that the latching mechanism 102 cannot move to unlatch the primary container 105 whenever the locking mechanism 101 and the needle cap 108 are in place. The locking mechanism 101 prevents the needle from accidentally being actuated during storage or transportation of the dose cassette, as well as when the dose cassette is being handled (e.g., when the dose cassette is being inserted into an autoinjector). Because the retraction latching mechanism 102 is biased by the spring 123, the spring could potentially become compressed, for example, if the dose cassette is dropped. If the spring 123 is compressed enough, the retraction latching mechanism 102 could become disengaged with the housing of the dose cassette, causing the needle to move. The locking mechanism ensures that such an event does not happen.

FIG. 13 is a sectioned perspective view of a portion of a dose cassette in accordance with the disclosed embodiments. The portion of the dose cassette in FIG. 13 shows a close up of the sectioned perspective view of the dose cassette of FIG. 12. The needle insertion and retraction latching mechanism 102 is biased radially towards the walls of the secondary container via a spring 123. Removing the needle cap 108 allows the lock mechanism 101 to be deactivated, such that the retraction latching mechanism 102 can move radially within the dose cassette. The spring 123 bias is overcome when the plunger head driver 610 pushes the latch off the secondary container housing ledge 122. The plunger head driver 610 pushes the retraction latching mechanism 102 via a ramp 115, visible in FIG. 14. In an alternative embodiment, the plunger head driver may have a ramp to push the retraction latching mechanism. In either embodiment, the plunger head driver and retraction latching mechanism are configured such that an axial movement of the plunger head driver can cause the retraction latching mechanism to move radially.

Figure 14:
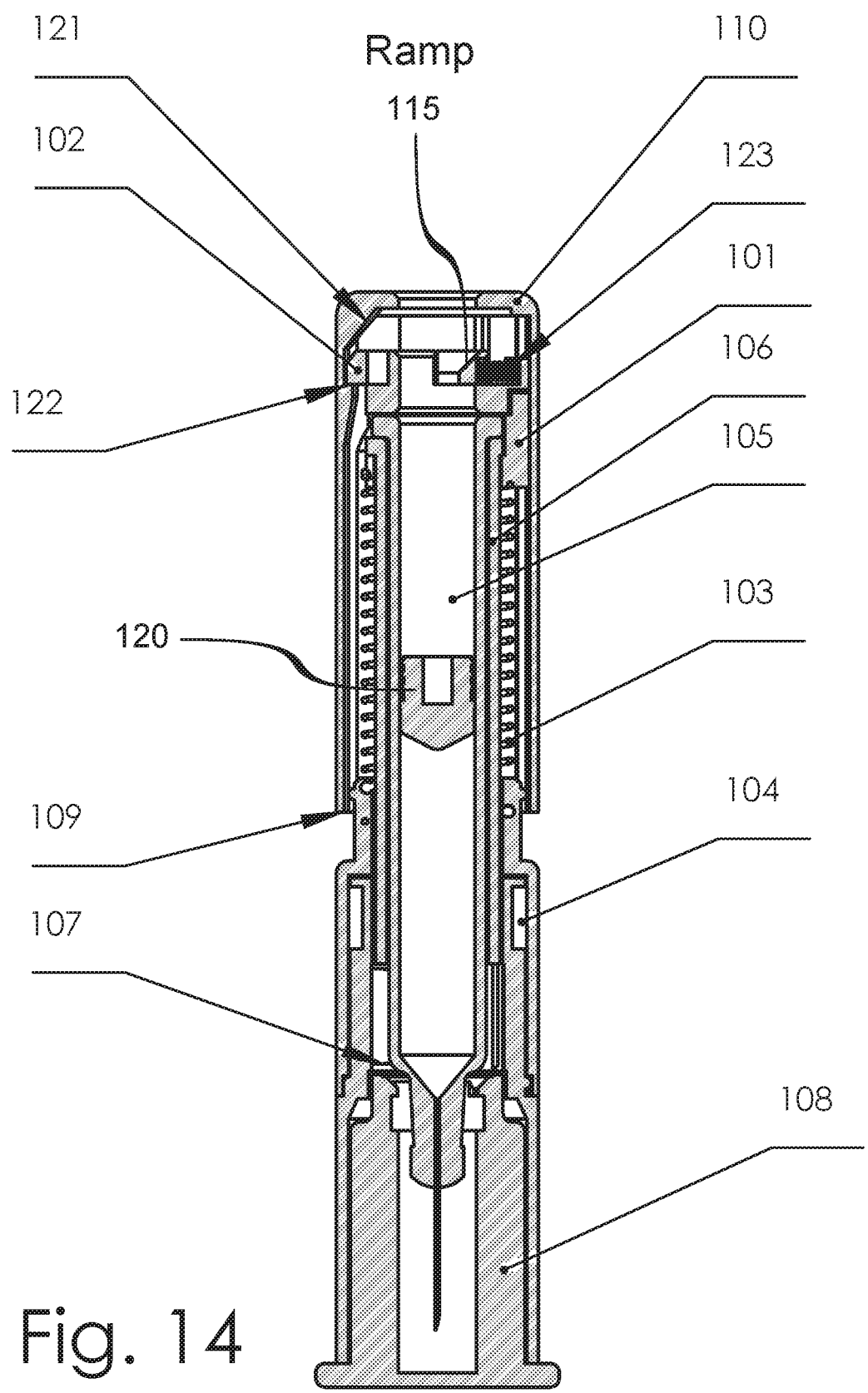
FIG. 14 is a cross section view of a dose cassette in accordance with the disclosed embodiments.

With the spring 103 biased distally, a rapid needle insertion is enacted when the latch of the retraction latching mechanism 102 is pushed off the secondary container housing ledge 122. In other words, when the retraction latching mechanism 102 no longer mechanically engages with the secondary container housing ledge 122, the spring 103 that is compressed pushes rapidly out of the dose cassette housing. The spring 103 also continues to bias the primary container 105 after the needle has been inserted so that the needle stays in position while a medicament is administered. The needle outside of the housing can be seen in FIGS. 25 and 26. The linear actuator 600 proceeds further distally beyond the retraction latching mechanism 102 to expelling the medicament. The dose is expelled by the plunger head driver 610 pushing a plunger head 120 of the dose cassette (the plunger head 120 is shown in FIG. 14). The needle may be inserted to a particular depth based on how the dose cassette is configured. For example, the primary container 105 may be configured with a wider diameter at the proximal end so that it cannot extend past a specific point, such as near the ledge 109 where the wider diameter portion of the primary container 105 may mechanically engage with the housing of the dose cassette. In another example, the distal end of the housing of the dose cassette may narrow such that the primary container 105 cannot move past that section of the housing. Accordingly, a needle may be controlled to only extend a predetermined amount outside of the dose cassette and/or autoinjector base. The spring 103 also keeps the primary container 105 and the needle biased distally When the full dose is expelled, the linear actuator moves proximally back to a home position, such as the position. During the return stroke, the plunger head driver 610 is coupled to the retraction latching mechanism 102, pulling the primary container assembly (the locking mechanism 101, the retraction latching mechanism 102, the primary container 105, primary container carrier 106) proximally into the dose cassette. This occurs because a surface opposite the ramp 115 (on a distal side of the retraction latching mechanism) mechanically engages with the plunger head driver 610 when it moves proximally through the dose cassette after the needle has been inserted and the dose has been expelled. Accordingly, the primary container assembly can move proximally and pull the needle out of the user and back into the dose cassette as the plunger head driver 610 moves proximally through the dose cassette.

As the plunger head driver 610 and the retraction latching mechanism 102 reaches the proximal-most end of the dose cassette, the latching mechanism 102 is pushed outward by a ramp 121 of the housing of the dose cassette, disengaging with the plunger head driver 610 so that the plunger head driver 610 and the retraction latching mechanism 102 become decoupled. The ledge 122 also has a ramp so that the latching mechanism can move past the ledge on the return stroke as well. The spring bias of both springs 123 and 103 reorient the primary container assembly back into their initial position once the plunger head driver 610 is released from interfering with the latching mechanism 102. In the initial position, as shown in FIGS. 12-14, the latching mechanism 102 rests on the dose cassette ledge 122. This secures the used needle within the dose cassette, and the dose cassette can then be safely ejected from an autoinjector without having an exposed needle.

FIG. 14 is a cross section view of a dose cassette in accordance with the disclosed embodiments. The dose cassette is similar to the dose cassette described above with respect to FIGS. 11-13, except the spring 103 is in a different location within the dose cassette. FIG. 14 shows the latching mechanism 102 that has a ramp 115. The ramp 115 is actuated by the plunger head driver 610, unlatching the latching mechanism 102 from the housing/outer container of the dose cassette at the ledge 122. FIG. 14 also shows the RFID tag 104 that can be read by an RFID reader, such as the RFID reader 750 of FIG. 9. FIG. 14 also shows the plunger 120 of the dose cassette that can be actuated by the plunger head driver 610 of an autoinjector to expel a dosage of medicament to a user.

Although the mechanisms for needle actuation described above are with respect to a needle in a disposable dose cassette, the aspects of the dose cassette can be implemented in a reusable autoinjector as well, whether the reusable autoinjector uses dose cassettes or not. That is, methods and aspects for securing, actuating, and retracting the needle as described herein are not limited to disposable dose cassettes. Accordingly, rapid needle insertion can occur as a feature of a primary drive mechanism used to deliver medicament in any type of injector, other embodiments of which are described below.

In various embodiments, during a resting state, the needle is retracted within the injector unit (a home position). A primary container is fixed to a primary container carrier, which is fixed to one end of a tension spring. The primary container carrier can move axially within the unit. In the home position, the spring is elongated, producing a force in the distal direction of the device. This position is maintained via a latching mechanism. The latching mechanism is spring biased toward a ledge. The ledge is perpendicular to the axial motion of the primary container carrier and rigidly attached to the unit. In various embodiments, the latching mechanism may move linearly or rotationally, but in either method the latching mechanism travels perpendicular to the primary axis and moves such that the latching mechanism no longer mechanically engages with the ledge. Accordingly, the latching mechanism is shaped such that the linear or rotational movement will cause the latching mechanism to disengage with the ledge. The ledge is preceded by a ramp, allowing the latching mechanism to slide up the ramp, against the spring force, and secure to the ledge.

To release the latch from the ledge, a linear actuator provides a ramp and hook. The linear actuator also provides a ledge, which is larger than the one rigidly attached to the unit. As the ramp moves distally, it contacts a section of the latch, sliding the latch free from the ledge. In another embodiment, a ramp may be on the latch instead of or in addition to the ramp on the linear actuator. In any case, the engagement of the linear actuator translates motion from the linear actuator into motion of the latch in a perpendicular direction to the motion of the linear actuator. The movement of the latch releases the tension spring, rapidly driving the primary container carrier distally. The carrier is stopped at a pre-determined distance via a mechanical barrier, depending on needle depth requirements.

As the linear actuator proceeds distally, expelling the medicament, the ramp and hook push the latching mechanism aside, and then proceeds beyond the contact point of the latch to engage a plunger. When the linear actuator retracts proximally within the device, the latching mechanism attaches to the hook on the linear actuator. The linear actuator overcomes the spring force, and the two components move distally together. Because the hook ledge is greater than that of the ledge on the unit, it allows the latching mechanism to slide over the ramp while remaining fixed to the hook on the linear actuator. A second ramp immediately proceeds the first, which is larger than the hook ledge. This causes the latch to be released from the hook. Upon release from the hook, the latch and primary container carrier springs return and secure the primary container to the home position ledge.

To prevent misfires if the unit is dropped or misused, additional design features may be included. For example, an embodiment includes a lock which mechanically engages with the latching mechanism. This lock is biased in place via the needle shield. When the lock is in place, the latching mechanism cannot be removed from the ledge, ensuring the spring force cannot be overcome if dropped or mishandled. Upon removal of the needle cap, the lock pulls away from the latching mechanism and the latch can then be released from the ledge.

In some embodiments, a second ramp and hook are on the linear actuator distally located from the first ramp and hook. In this embodiment, if the latch detaches from the ledge accidentally, the primary container carrier proceeds to engage and get caught on the secondary hook. The secondary hook is located such that the needle is still distally located within the device to prevent a needle stick injury. Sensors within the device can detect this anomaly and reset the latch by moving the linear actuator distally, and replacing the latch onto the ledge.

This secondary ramp and hook can also provide a way to remove a rigid needle shield. As the first ramp removes the latch from the ledge, the primary container carrier proceeds to the second hook. Meanwhile, this pushes the rigid needle shield through an elastomeric iris. As the linear actuator returns distally, the iris affixes to the needle shield, pulling it from the syringe. The linear actuator then proceeds distally and replaces the latch onto the ledge.

FIG. 15 is a sectioned perspective view of a reusable autoinjector base and a dose cassette 100 just prior to the dose cassette being inserted into the reusable autoinjector base in accordance with the disclosed embodiments. FIG. 15 shows a dose cassette 100, a backplate 810, a plunger head driver 610, a base latch 850, and a latch lock 870. In FIG. 15, the dose cassette 100 is about to be inserted into the autoinjector base. The dose cassette 100 may be a dose cassette such as the one described above with respect to FIGS. 11-14. The autoinjector base may be an autoinjector base such as the one described above with respect to FIGS. 9 and 10 having a linear actuator such as the one described above with respect to FIGS. 4-8. FIGS. 16-30 discussed below demonstrate the various states of a dose cassette and autoinjector according to an embodiment of the present technology.

FIG. 16 is a sectioned perspective view during an insertion of a dose cassette into a reusable autoinjector base in accordance with the disclosed embodiments. FIG. 16 shows the dose cassette 100 moving into the reusable autoinjector base. As the dose cassette is inserted, the base latch 850 moves radially toward the housing of the autoinjector base. This allows the dose cassette to be fully inserted into the autoinjector base. The base latch 850 includes a ramp 851 that engages with the dose cassette as the dose cassette is inserted. This interaction pushes the base latch 850 outward radially allowing the dose cassette to continue to move axially within the autoinjector base.

FIG. 17 is a sectioned perspective view of a dose cassette locked into a reusable autoinjector base in accordance with the disclosed embodiments. FIG. 17 shows the dose cassette after it has been pushed into the autoinjector base. A portion of the base latch 850 slides past the ledge 109 into a space where the dose cassette has a smaller diameter than the rest of the dose cassette. A locking surface 852 on the base latch 850 mechanically engages with a surface of the ledge 109 to lock the dose cassette in place with respect to the clasp mechanism of the autoinjector. In this way, as described herein, the dose cassette is secured within the autoinjector but can also be moved radially within the autoinjector along with the clasp mechanism. FIG. 17 also shows a sensor 830 and a needle cap 108. In addition, once fully inserted, a proximal end of the dose cassette bumps up against a backplate 810, causing a backplate spring 815 to be compressed. This spring biases the backplate 810 against the dose cassette, which pushes up against the base latch 850 such that the dose cassette is secured within the autoinjector base.

Figure 18:
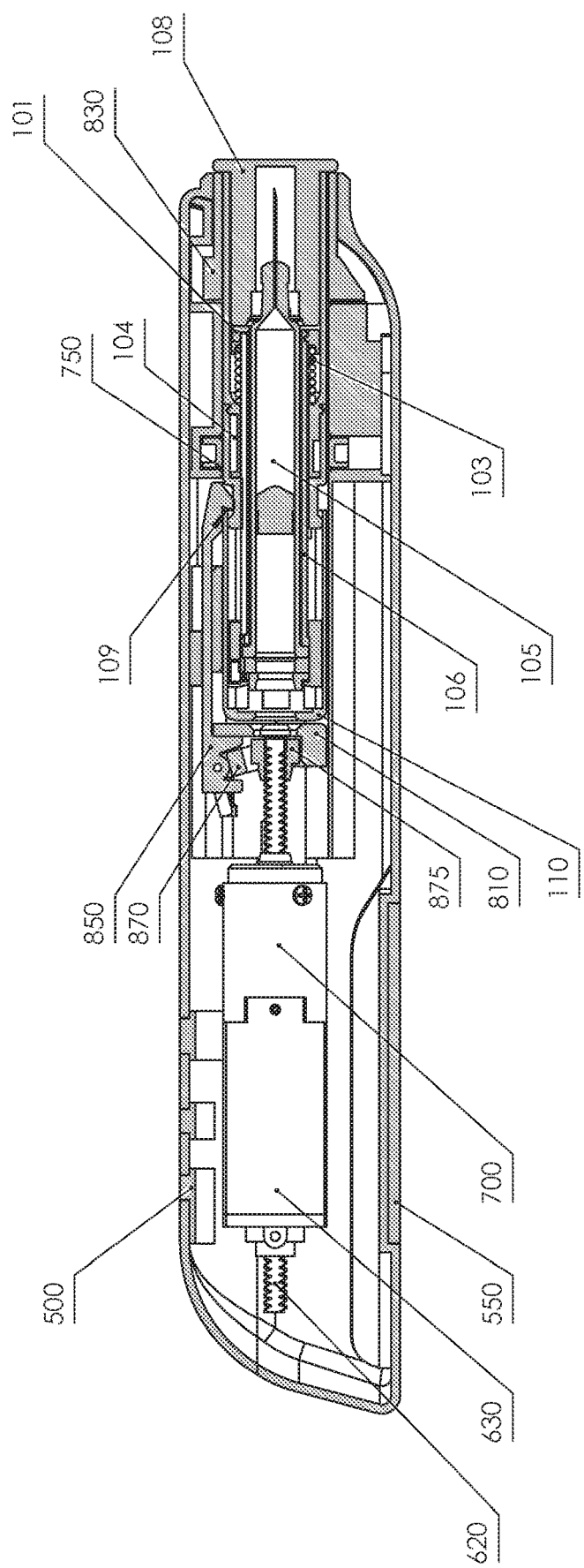
FIG. 18 is a cross section view of a dose cassette locked into a reusable autoinjector base in accordance with the disclosed embodiments.

FIG. 18 is a cross section view of a dose cassette locked into a reusable autoinjector base in accordance with the disclosed embodiments. The dose cassette is shown as being fully inserted in the autoinjector base, and the base latch 850 is in position to secure the dose cassette. At this point, no injection has taken place and the needle cap of the dose cassette is still covering the needle in the dose cassette. A plunger drive unit 610 is also shown engaging the latch lock center 875. As described herein, this allows the plunger drive unit 610 to rotate the latch lock 870 and move the clasp mechanism and dose cassette axially within the autoinjector base. FIG. 18 also shows how the RFID tag 104 of the dose cassette can align with the RFID tag reader 750 so that the information stored on the RFID tag 104 can be read.

Figure 19:
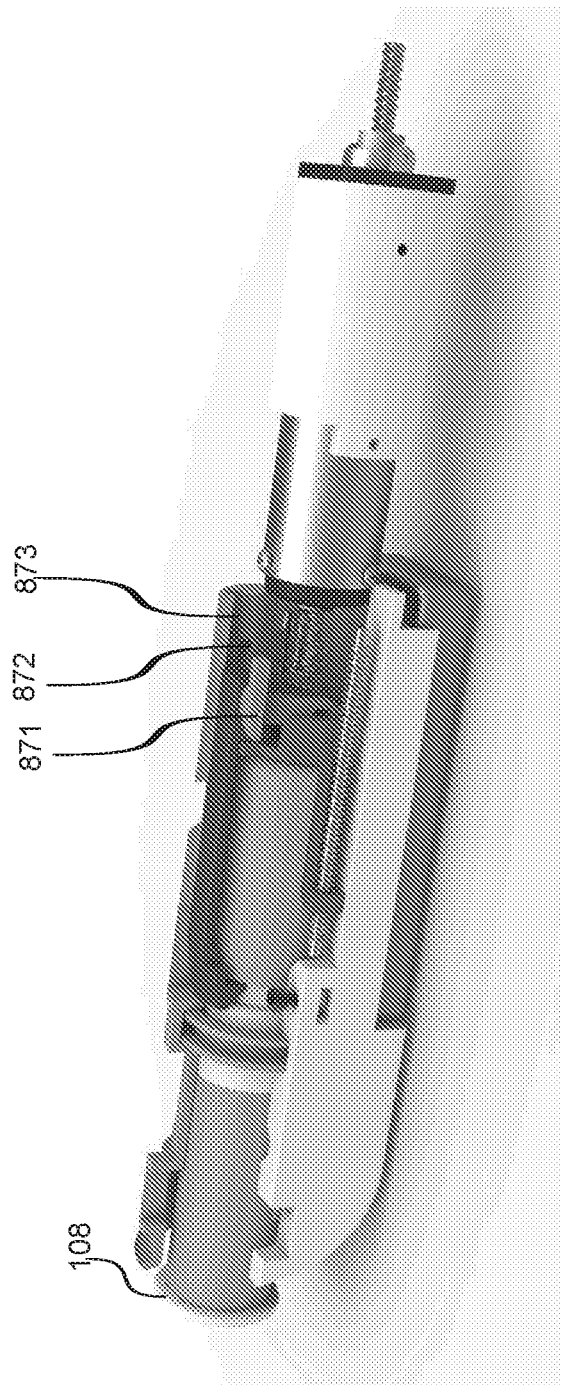
FIG. 19 is a sectioned perspective view of a dose cassette within a housing of a reusable autoinjector base in accordance with the disclosed embodiments.

FIG. 19 is a sectioned perspective view of a dose cassette within a housing of a reusable autoinjector base in accordance with the disclosed embodiments. FIG. 19 shows that a plunger drive unit has started to pull the latch lock center proximally within the housing, causing the latch lock 870 to rotate around a hinge 871. This causes a locking arm of the latch lock 870 to move out of a locking space 872 and into an unlocked space 873. Once the locking arm of the latch lock 870 is in in the unlocked space 873, the clasp mechanism including the latch lock 870 and the base latch 850 can move proximally within the housing as shown in FIGS. 20-23. This in turn also moves the dose cassette because the base latch 850 secures the dose cassette.

Figure 20:
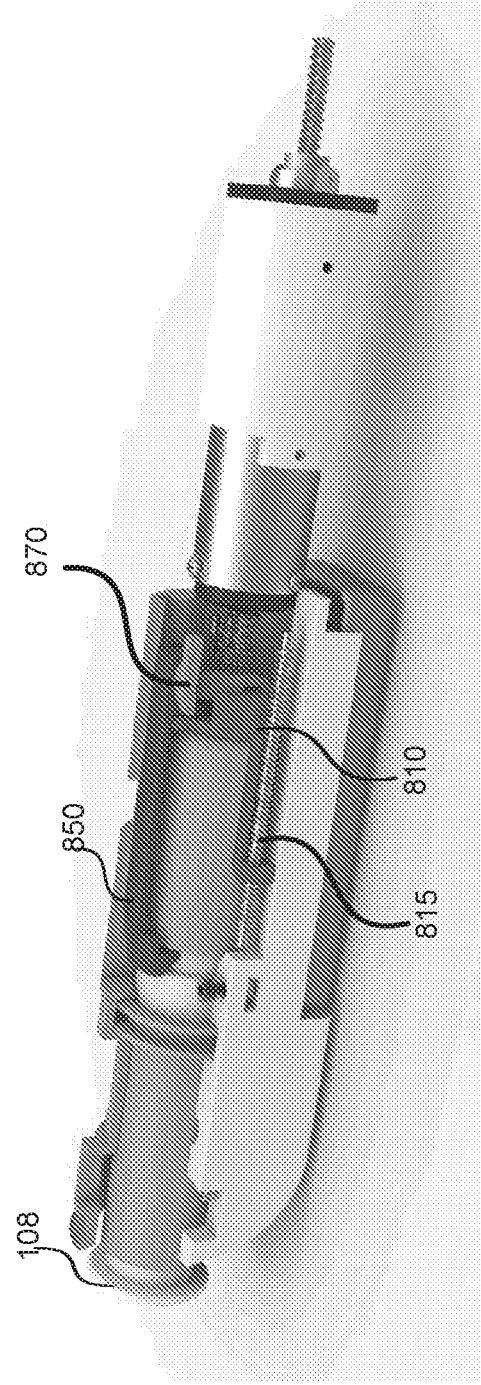
FIG. 20 is a sectioned perspective view of a needle cap of a dose cassette beginning to be removed in accordance with the disclosed embodiments.

FIG. 20 is a sectioned perspective view of a needle cap of a dose cassette beginning to be removed in accordance with the disclosed embodiments. FIG. 20 shows the clasp mechanism including the base latch 850 and the latch lock 870 having moved proximally within the autoinjector, such that needle cap 108 begins to be separated from the dose cassette because of mechanical engagement with a distal end of the housing. In this case, the distal end of the housing includes a sensor 830, but other embodiments may not have a sensor at the distal end of the housing where the needle cap mechanically engages with the housing. In this example, the sensor 830 is a proximity sensor that can detect a presence of the needle cap. Once the needle cap is fully inserted the autoinjector, the system may determine that a needle cap removal process may begin based on a signal from the sensor 830 indicating that a needle cap is present. As described herein, the needle cap 108 has a diameter that is larger than the diameter of the dose cassette. In this way, the dose cassette can slide into the housing but the needle cap 108 mechanically engages with the housing of the autoinjector base. FIG. 20 also shows that the baseplate 810 moves proximally along with the dose cassette, compressing the spring 815.

FIG. 21 is a sectioned perspective view of a needle cap of a dose cassette contacting a sensor of a reusable autoinjector base in accordance with the disclosed embodiments. FIG. 21 is similar to FIG. 20 but shows the sensor 830 and a spring 831 that biases the sensor 830 distally. When the dose cassette is pulled backward, the needle cap 108 mechanically engages with the sensor 830, causing it to move proximally as shown in FIG. 21. This spring can help the needle cap 108 be removed briskly once it has been pushed far enough out of the dose cassette.

FIG. 22 is a sectioned perspective view of a needle cap of a dose cassette being removed in accordance with the disclosed embodiments. Once the needle cap is removed as shown in FIG. 22, the spring 831 pushes the sensor 830 back forward. Accordingly, as shown in FIGS. 19-23, an autoinjector with a housing for disposable dose cassettes can be loaded. The dose cassette includes a primary container and needle, a secondary container, and a needle cap, the needle cap including a needle shield connected to a rigid base with a diameter larger than the secondary container of the dose cassette. When the dose cassette is loaded into the autoinjector housing, the outer edge of the rigid base makes contact with the pressure sensor surrounding the distal end of the housing. The autoinjector detects the presence of the needle cap via contact between the outer edge of the rigid base and the pressure sensor on the distal end of the housing. The autoinjector moves the dose cassette proximally within the housing of the autoinjector, separating the needle cap from the dose cassette when the proximal movement of the needle cap is impeded by contact between the outer edge of the rigid base and the pressure sensor on the distal end of the housing. The autoinjector then detects the absence of the needle cap via a loss of contact between the rigid base and pressure sensor when the needle cap is separated from the dose cassette. The autoinjector can then be activated for injection once the pressure sensor loses contact with the outer edge of the rigid base, confirming the needle cap has been removed from the dose cassette.

Figure 23:
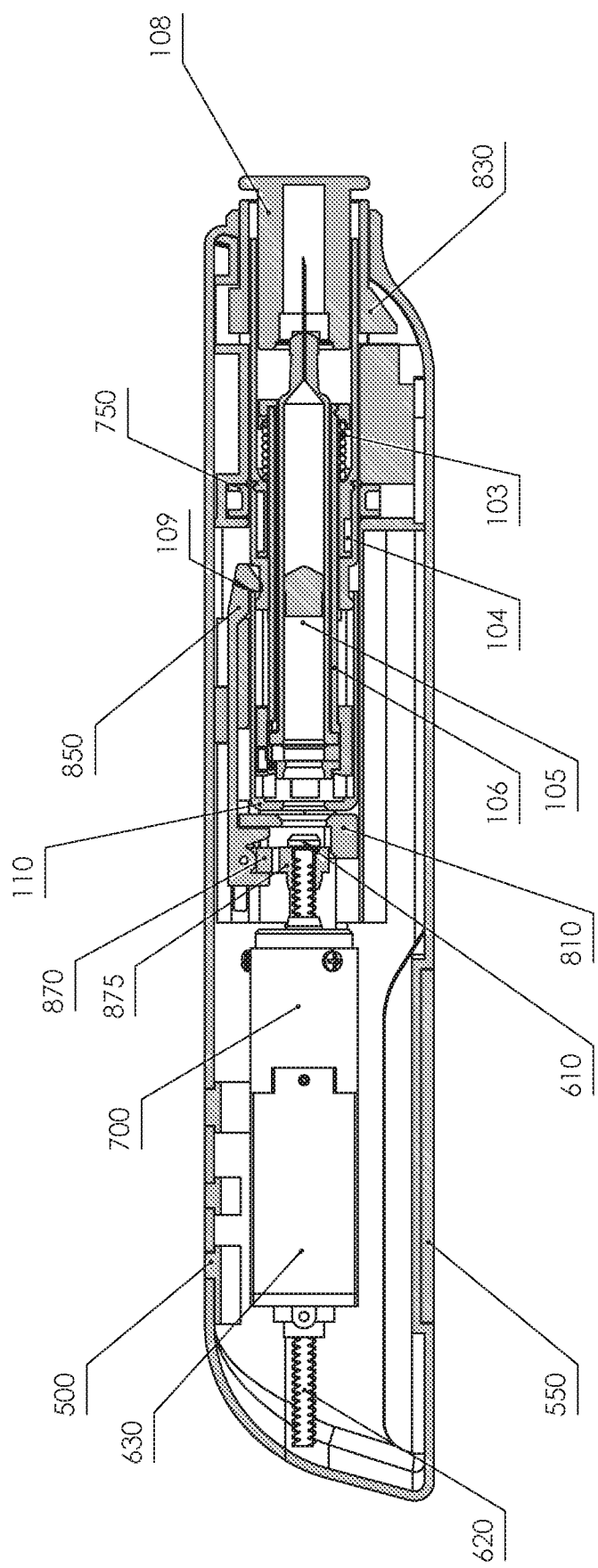
FIG. 23 is a cross section view of a needle cap of a dose cassette being removed in accordance with the disclosed embodiments.

FIG. 23 is a cross section view of a needle cap of a dose cassette being removed in accordance with the disclosed embodiments. It shows the dose cassette 108 beginning to be removed, similar to FIGS. 20 and 21, and shows the latch lock 870 in a rotated, unlocked state that allows for the clasp mechanism to move axially within the housing, so that the dose cassette can be moved for needle cap removal.

FIG. 24 is a sectioned perspective view of a dose cassette locked in place in advance of a needle protruding from the dose cassette in accordance with the disclosed embodiments. The needle cap in FIG. 24 has been removed, and the latch lock 870 has returned to a locked state, as the locking arm of the latch lock 870 has moved back into the locking space 872 and out of the unlocked space 873.

FIG. 25 is a sectioned perspective view of a needle protruding from a dose cassette in accordance with the disclosed embodiments. The plunger head driver of the linear actuator can proceed into the dose cassette to actuate needle insertion as described herein. FIG. 25 shows a needle 130 extending from the autoinjector base.

Figure 26:
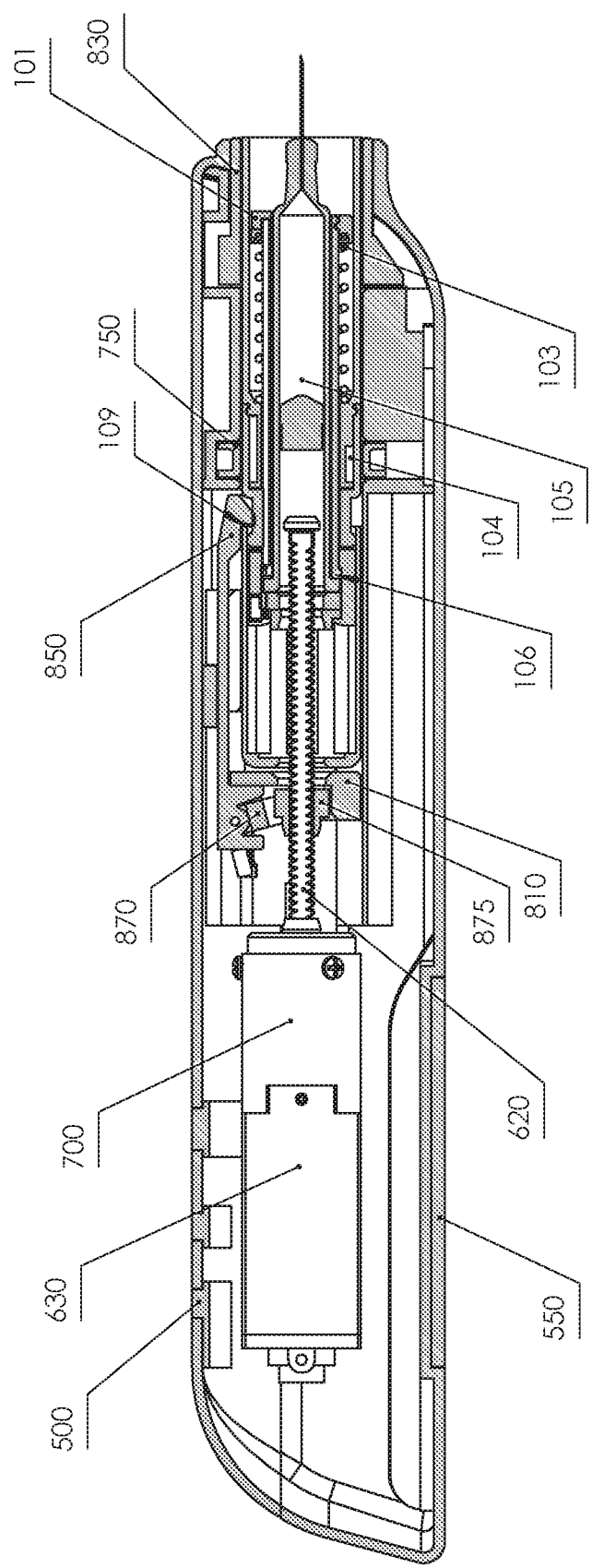
FIG. 26 is a cross section view of a needle protruding from a dose cassette in accordance with the disclosed embodiments.

FIG. 26 is a cross section view of a needle protruding from a dose cassette in accordance with the disclosed embodiments. The lead screw 620 in FIG. 26 can be seen extending into the dose cassette to actuate the needle 130 insertion. Although the plunger head driver 610 has not yet engaged a plunger to deliver the medicament, the plunger head driver 610 can move distally even further to engage the plunger and deliver the medicament being stored in the primary container 105 through the extended needle 130. FIG. 26 also shows the latch lock 870 in a locked state.

Figure 27:
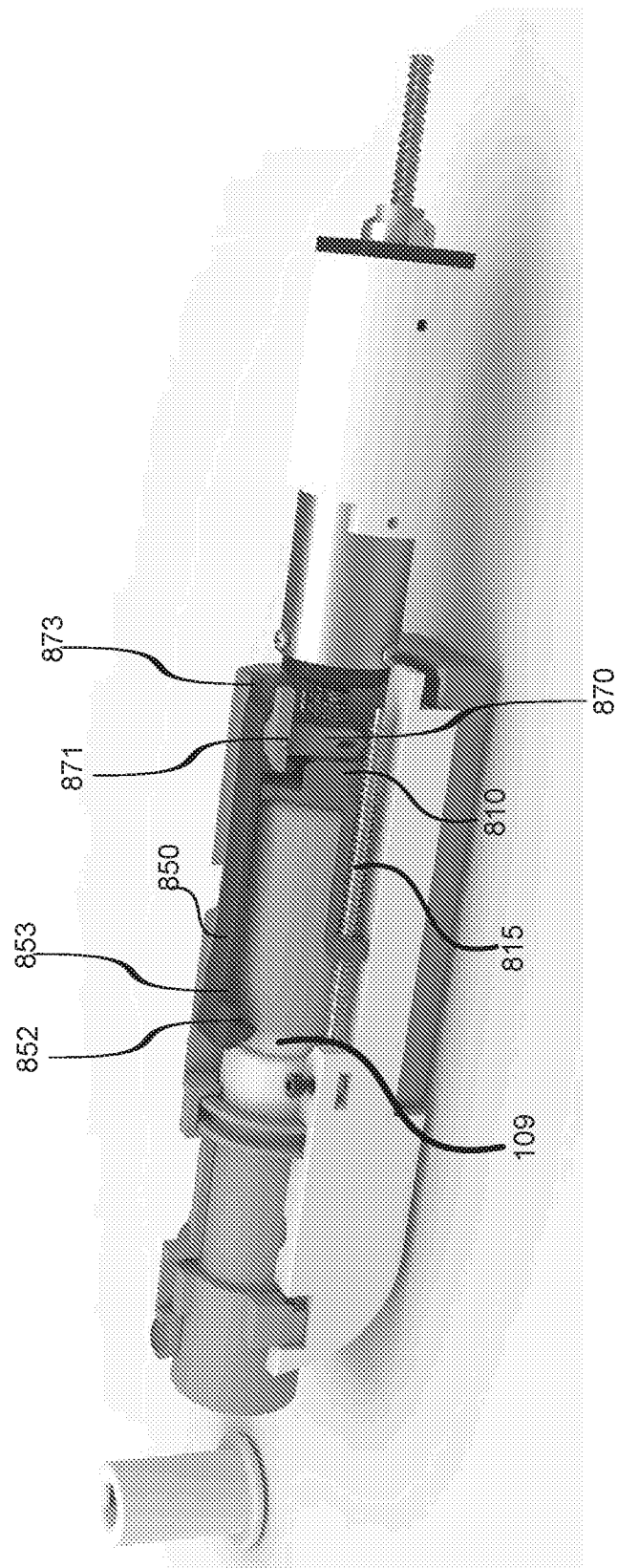
FIG. 27 is a sectioned perspective view of a dose cassette being unlocked from a reusable autoinjector base in accordance with the disclosed embodiments.

FIG. 27 is a sectioned perspective view of a dose cassette being unlocked from a reusable autoinjector base in accordance with the disclosed embodiments. In FIG. 27, the latch lock 870 is again rotated around a hinge 871 when the linear actuator pulls the plunger head driver 610 proximally so that it mechanically engages with the latch lock center 875. This again causes the locking arm of the latch lock 870 to move into the unlocked space 873. In addition, the base latch 850, the dose cassette, and the backplate 810 are also moved proximally within the housing. In FIG. 27, the latch lock 870, the base latch 850, the dose cassette, and the backplate 810 are moved proximally further than they were for the needle cap removal as shown in FIGS. 19-23. This causes a ramp 853 of the base latch 850 to mechanically engages with part of the housing of the autoinjector to unlatch the base latch 850. During needle cap removal, the ramp 853 does not mechanically engages with the housing, so the dose cassette stays secured by the base latch 850. This is why the base latch 850 is moved further in a proximal direction in order to unlatch the dose cassette after injection. FIG. 27 also demonstrates how this mechanical engagement between the ramp 853 and the housing causes the locking surface 852 of the base latch 850 to become disengaged with the ledge 109, thereby unlatching the dose cassette from the autoinjector base. The movement of the backplate 810 as the dose cassette is pulled back also further compresses the spring 815, storing compression energy that is used to eject the dose cassette as described herein (and shown for example in FIGS. 29 and 30).

Figure 28:
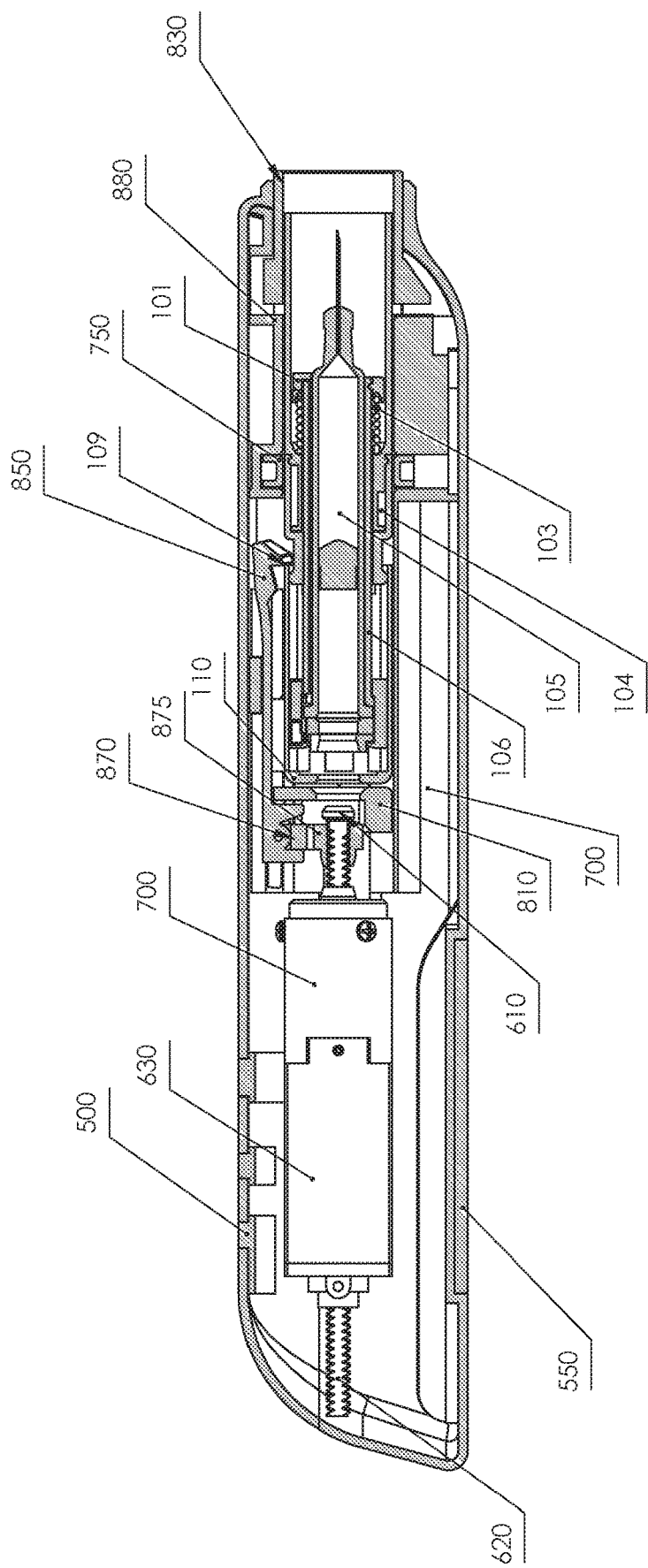
FIG. 28 is a cross section view of a dose cassette being unlocked from a reusable autoinjector base in accordance with the disclosed embodiments.

FIG. 28 is a cross section view of a dose cassette being unlocked from a reusable autoinjector base in accordance with the disclosed embodiments. FIG. 28 shows the mechanical engagement of a ramp of the base latch 850 with the housing of the autoinjector, causing the base latch 850 to move radially away from the dose cassette and disengage from the ledge 109. FIG. 28 also shows how the plunger head driver 610 is engaged with the latch lock center 875 to pull each of the latch lock center 875, the latch lock 870, the base latch 850, and the dose cassette proximally to a position further proximal than the position at which the needle cap was removed (as shown for example in FIG. 23). Also shown is how the needle has been pulled back into the dose cassette housing after injection.

FIG. 29 is a sectioned perspective view of a dose cassette 100 being ejected from a reusable autoinjector base in accordance with the disclosed embodiments. FIG. 30 is a sectioned perspective view of an ejected dose cassette 100 in accordance with the disclosed embodiments. After the base latch 850 becomes disengaged from the dose cassette 100 as described above with respect to FIGS. 27 and 28, the dose cassette 100 is ejected as a result of the spring 815 pushing the backplate 810 distally, which also then pushes the dose cassette 100 distally. As described above, the needle is withdrawn back into the dose cassette before ejection such that the dose cassette may be safely disposed of. After full ejection as shown in FIG. 30, the autoinjector is returned back to a position such as that shown in FIGS. 9 and 15, so that it can receive a subsequent dose cassette. To do so, the plunger head driver 610 moves proximally, allowing the latch lock to be pushed proximally by the spring 820 and return to a locked position.

FIG. 31 is a flow diagram illustrating a method 3100 for utilizing a linear actuator with a hollow drive shaft in accordance with the disclosed embodiments. In various embodiments, fewer, additional, and/or different operations may be performed. Also, the use of a flow diagram is not meant to be limiting with respect to the order of operations performed unless otherwise noted. In an operation 3105, a hollow drive shaft is rotated by a motor. The hollow drive shaft and motor may be similar to those described herein, such as with respect to FIGS. 4-8 above. In an operation 3110, a lead screw nut is rotated in response to rotation of the hollow drive shaft. The lead screw nut is operably connected to the hollow drive shaft. The lead screw nut may be connected to the hollow drive shaft directly or through a gear box.

In an operation 3115, the lead screw is moved in response to the rotation of the lead screw nut. The lead screw is operably connected to the lead screw nut. In particular, the threads of the lead screw engage with the lead screw nut so that the lead screw can move axially within the lead screw nut. This can therefore translate rotational motion from the motor into linear motion of the lead screw. As described herein, the rotation of the lead screw nut can also include exerting, from the hollow drive shaft, a rotational force on the lead screw nut via a gear box operably connected to the hollow drive shaft and the lead screw nut. As described herein, the lead screw is configured to pass through all or at least part of the hollow drive shaft. The gear box may also include a hollow gear box opening, that allows the lead screw to pass through all or part of the hollow gear box opening. This hollow gear box opening is aligned with the hollow drive shaft as described herein. The lead screw may pass through an entire length of each of the hollow gear box opening and the hollow drive shaft, even extending outside of the hollow gear box opening and hollow drive shaft combined.

As described herein, the lead screw can have a plunger head driver at its distal end. Therefore, using rotation of the motor causing movement of the lead screw, the various methods and systems disclosed herein can be practiced, including, e.g., automated needle cap removal, automated rapid needle insertion, medicament expulsion, automated dose cassette ejection, and any combination thereof. The motor may also be controlled by a controller that can send signals to the motor to control aspects of the motor such as speed at which to rotate, which direction to rotate, etc. In this way, the motor can be controlled to implement the various methods and systems described herein.

Figure 32:
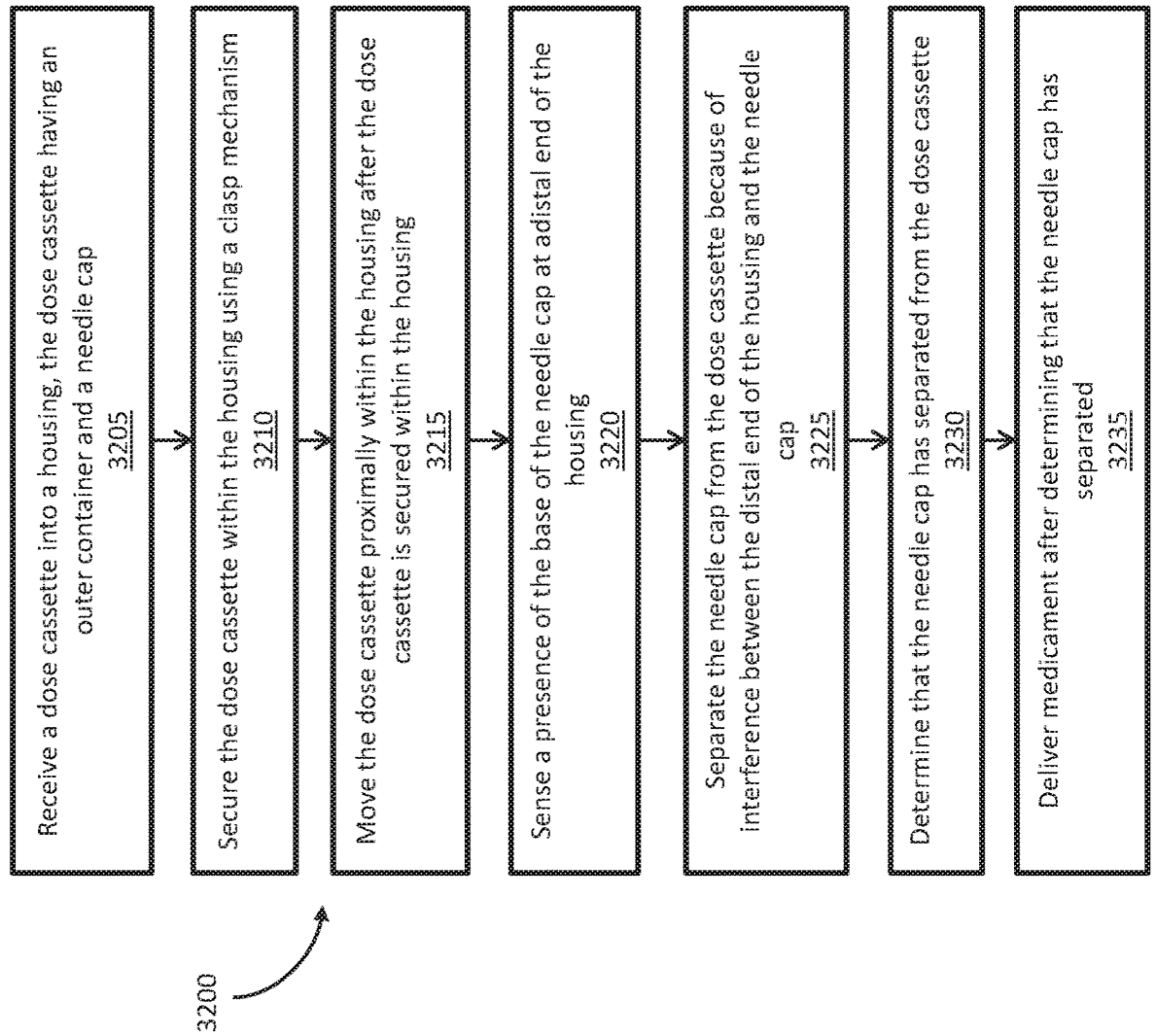
FIG. 32 is a flow diagram illustrating a method for removing a needle cap from a dose cassette in accordance with the disclosed embodiments.

FIG. 32 is a flow diagram illustrating a method 3200 for removing a needle cap from a dose cassette in accordance with the disclosed embodiments. In various embodiments, fewer, additional, and/or different operations may be performed. Also, the use of a flow diagram is not meant to be limiting with respect to the order of operations performed unless otherwise noted. In an operation 3205, a dose cassette is received into a housing. The dose cassette includes an outer container and a needle cap having a base with a diameter larger than the outer container. In an operation 3210, the dose cassette is secured within the housing using a clasp mechanism as described herein. Although specific clasp mechanisms are described above, any mechanism suitable for securing the dose cassette within the housing may be utilized.

In an operation 3215, the dose cassette is moved proximally within the housing after the dose cassette is secured within the housing. In an operation 3220, a presence of the base of the needle cap at the distal end of the housing is sensed. In some embodiments, the presence of the needle cap may not be detected. Once the presence of the needle cap is sensed, the needle cap is separated from the dose cassette because of mechanical engagement between a distal end of the housing and the needle cap in an operation 3225. In some embodiments, the needle cap may be removed only after the needle cap is sensed.

In an operation 3230, it is determined that the needle cap has separated from the dose cassette. This sensing may utilize the same sensor used in the operation 3220, or may utilize a different sensor. The sensor(s) used to determine presence or absence of a needle cap may also be utilized to determine the presence of skin after the needle cap is removed. In this way, an autoinjector can determine that, after a needle cap is removed, the autoinjector is in proper position for an injection. In some embodiments, the autoinjector will not initiate the rapid needle insertion disclosed herein unless skin is sensed. In an operation 3235, medicament of the dose cassette is delivered after determining that the needle cap has separated from the dose cassette.

Figure 33:
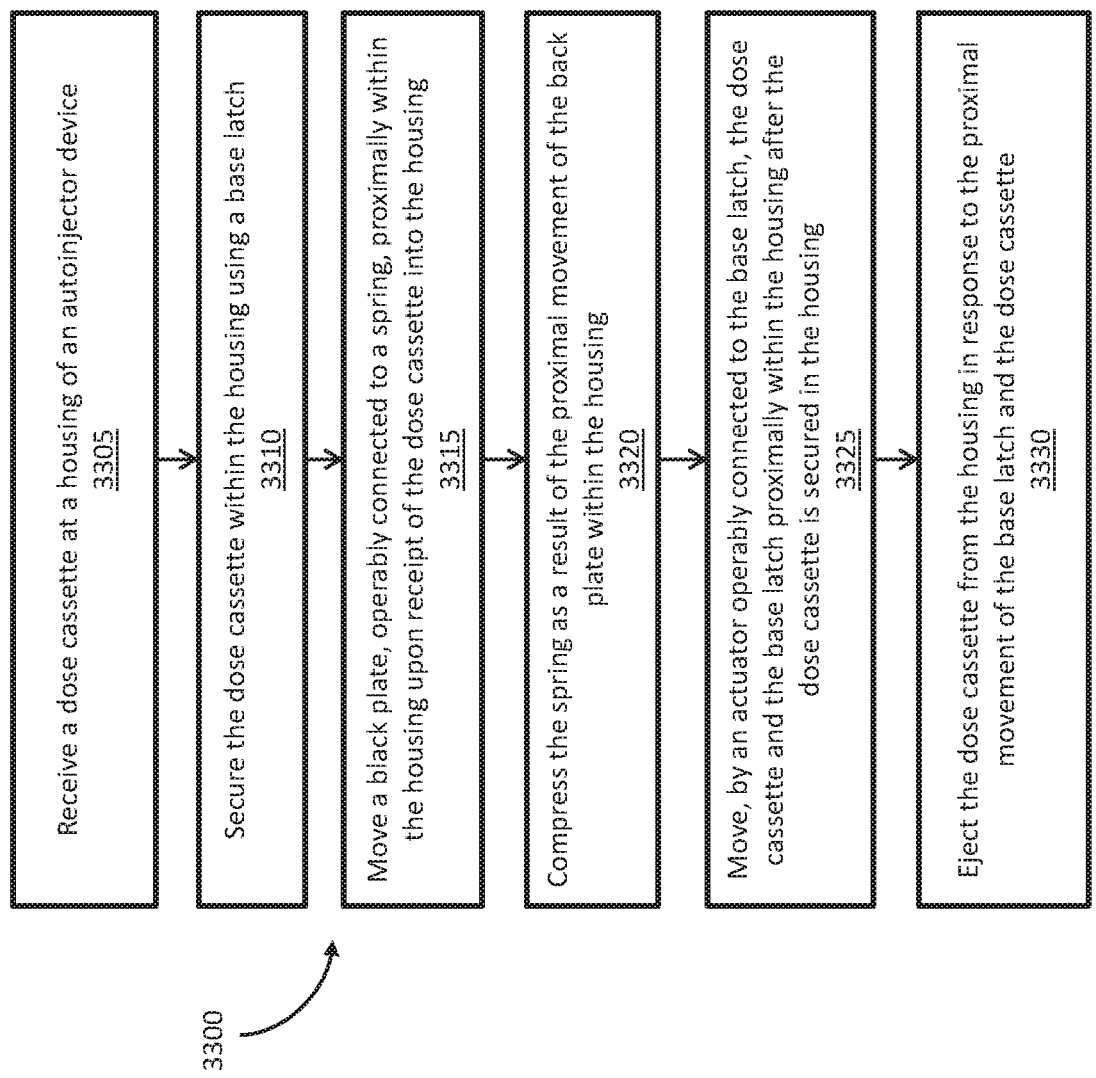
FIG. 33 is a flow diagram illustrating a method for ejecting a dose cassette from a reusable autoinjector base in accordance with the disclosed embodiments.

FIG. 33 is a flow diagram illustrating a method 3300 for ejecting a dose cassette from a reusable autoinjector base in accordance with the disclosed embodiments. In various embodiments, fewer, additional, and/or different operations may be performed. Also, the use of a flow diagram is not meant to be limiting with respect to the order of operations performed unless otherwise noted. In an operation 3305, a dose cassette is received at a housing of an autoinjector device. In an operation 3310, the dose cassette is secured within the housing using a base latch. In an operation 3315, a black plate operably connected to a spring is moved. The back plate moves proximally within the housing upon receipt of the dose cassette into the housing.

In an operation 3320, the spring is compressed as a result of the proximal movement of the back plate within the housing. In an operation 3325, the dose cassette is moved by an actuator operably connected to the base latch. The movement of the dose cassette and the base latch is proximally within the housing after the dose cassette is secured in the housing. In an operation 3330, the dose cassette is ejected from the housing in response to the proximal movement of the base latch and the dose cassette. The ejection of the dose cassette can be effected using the method 3400 described below with respect to FIG. 34.

Figure 34:
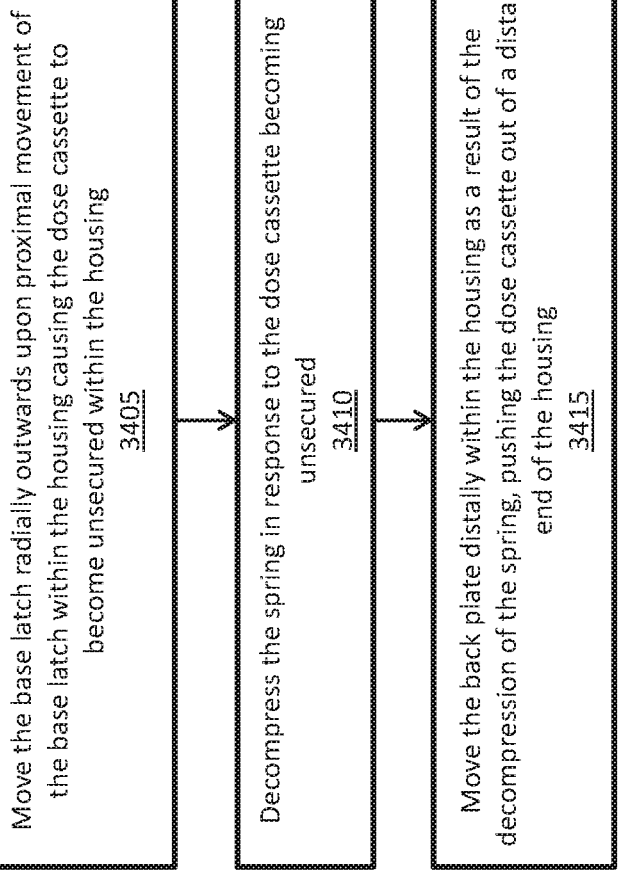
FIG. 34 is a flow diagram illustrating a method for unlocking a dose cassette from a reusable autoinjector base in accordance with the disclosed embodiments.

FIG. 34 is a flow diagram illustrating a method 3400 for unlocking a dose cassette from a reusable autoinjector base in accordance with the disclosed embodiments. In various embodiments, fewer, additional, and/or different operations may be performed. Also, the use of a flow diagram is not meant to be limiting with respect to the order of operations performed unless otherwise noted. In an operation 3405, the base latch moves radially outwards because of proximal axial movement of the base latch within the housing. The movement of the base latch causes the dose cassette to become unsecured within the housing. In an operation 3410, the spring attached to the backplate is decompressed in response to the dose cassette becoming unsecured. In an operation 3415, the back plate moves distally within the housing as a result of the decompression of the spring, wherein the movement of the back plate pushes the dose cassette out of a distal end of the housing.

As described herein the base latch may include a first ramp surface that mechanically engages with the housing to cause the base latch to move radially outwards upon the proximal movement of the dose cassette within the housing. The radially outward movement of the base latch causes a locking surface of the base latch to move out of contact with a ledge of the dose cassette. The base latch may also include a second ramp surface. During an insertion of the dose cassette, an outer container of the dose cassette mechanically engages with the second ramp surface and pushes the base latch radially outward until the locking surface of the base latch reaches the ledge. Upon reaching the ledge, the distal end of the base latch moves radially inward into a space in the outer container of the dose cassette at the ledge. The autoinjector may also include a latch lock operably connected to the base latch. The latch lock prevents the base latch from moving axially within the housing while the dose cassette is being received into the housing.

The latch lock may be adjusted as described herein, in response to the securing of the dose cassette within the housing, such that the base latch is permitted to move axially within the housing. This allows for moving the base latch and the dose cassette proximally within the housing from a first position to a second position or a third position. At the first position the base latch secures the dose cassette within the housing upon full insertion of the dose cassette. At the second position a needle cap on a distal end of the dose cassette mechanically engages with a distal end of the housing such that the needle cap is removed from the dose cassette. At the third position, the base latch mechanically engages with the housing and moves radially outwards to unlock the dose cassette as described herein. A first distance between the first position and second position is less than a second distance between the first position and the third position.

A medicament stored within the dose cassette can be delivered after the dose cassette is secured within the housing. In some embodiments, the dose cassette may be ejected from the housing only after the medicament is delivered.

Figure 35:
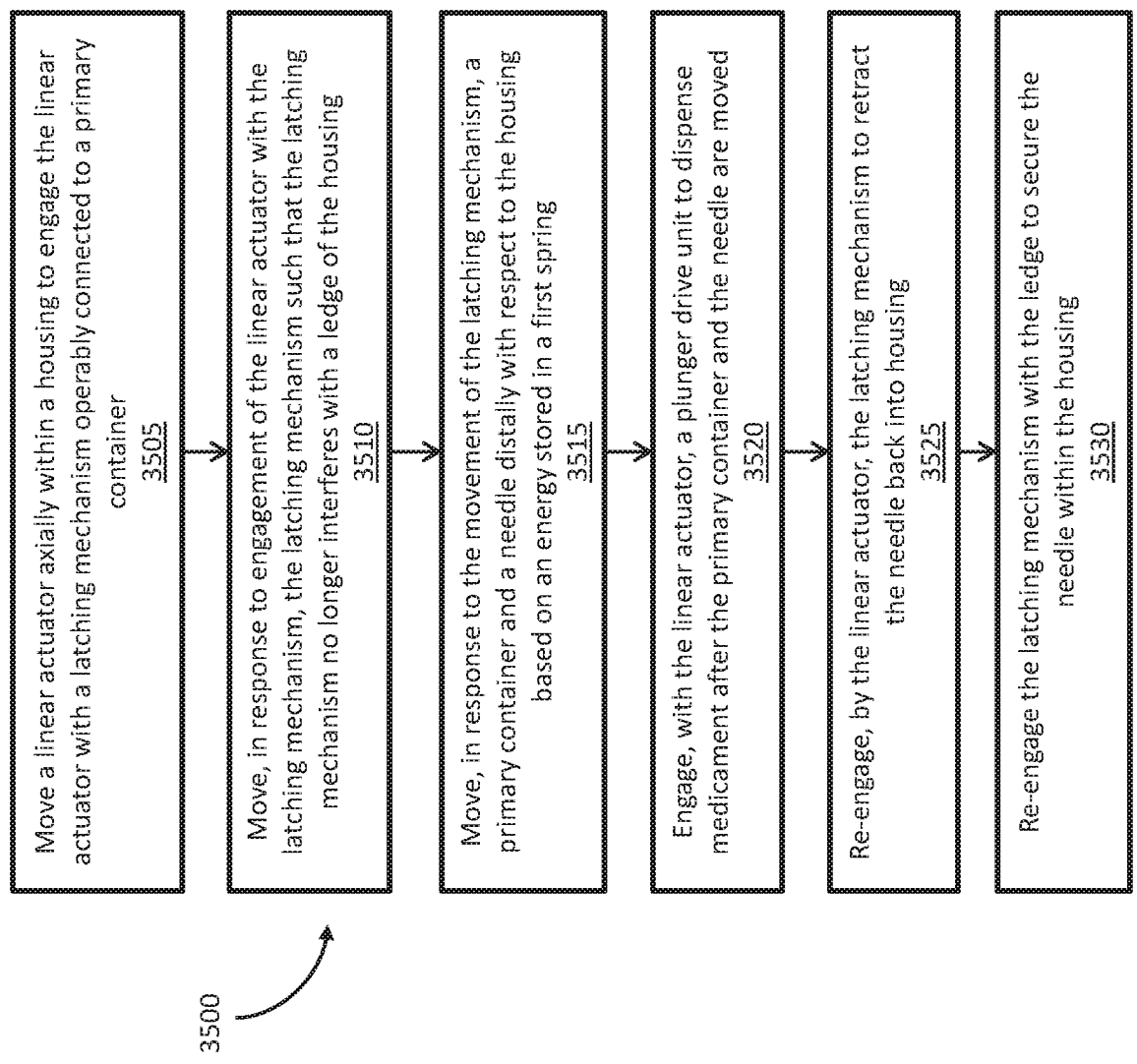
FIG. 35 is a flow diagram illustrating a method for needle insertion from a dose cassette in accordance with the disclosed embodiments.

FIG. 35 is a flow diagram illustrating a method 3500 for needle insertion from a dose cassette in accordance with the disclosed embodiments. In various embodiments, fewer, additional, and/or different operations may be performed. Also, the use of a flow diagram is not meant to be limiting with respect to the order of operations performed unless otherwise noted. In an operation 3505, a linear actuator is moved axially within a housing to engage the linear actuator with a latching mechanism operably connected to a primary container. The primary container is operably connected to a needle and is configured to move axially within the housing. A first spring has a first end operably connected to the primary container and a second end operably connected to the housing. An axis of the first spring may be oriented parallel to an axis in which the primary housing moves within the housing of an autoinjector base, so that energy stored by the spring can be applied to move the primary housing. The latching mechanism is operably connected to the primary container and is biased toward a ledge by a second spring. The latching mechanism may also include a ramp oriented at an angle between an axis in which the linear actuator moves and a surface of the ledge perpendicular to the axis, such that when the linear actuator engages the latching mechanism, the latching mechanism moves in a plane perpendicular to the axis. In another embodiment, a distal end of the linear actuator includes a ramp oriented at an angle between an axis in which the linear actuator moves and a surface of the ledge perpendicular to the axis, such that when the linear actuator engages the latching mechanism, the latching mechanism moves in a plane perpendicular to the axis. The ledge is fixed with respect to the housing. A surface of the ledge may be oriented perpendicular to the axial direction of movement of the primary container within the housing. The second spring has a first end operably connected to the latching mechanism and a second end operably connected to the primary container. An axis of the second spring may be oriented perpendicular to an axis in which the primary container moves within the housing of the autoinjector base, so that the latching mechanism can move perpendicular to the movement of the primary container based on energy stored in the second spring. The primary container and the needle are fixed within the housing based on mechanical engagement between the latching mechanism and the ledge before the linear actuator is engaged with the latching mechanism.

In an operation 3510, the latching mechanism is moved in response to engagement of the linear actuator with the latching mechanism, such that the latching mechanism no longer mechanically engages with the ledge. In an operation 3515, the primary container and the needle are moved in response to the movement of the latching mechanism. In particular, the primary container and the needle are moved distally with respect to the housing based on an energy stored in the first spring.

In an operation 3520, the linear actuator engages a plunger drive unit to dispense the medicament after the primary container and the needle are moved based on the energy stored in the first spring. In an operation 3525, the latching mechanism is re-engaged by the linear actuator to retract the needle back into housing. In an operation 3530, the latching mechanism is re-engaged with the ledge to secure the needle within the housing. The housing may include a ramp configured to move the latching mechanism such that the latching mechanism and linear actuator disengage based on distal movement of the linear actuator, and after the needle is retracted back into the housing.

Figure 36:
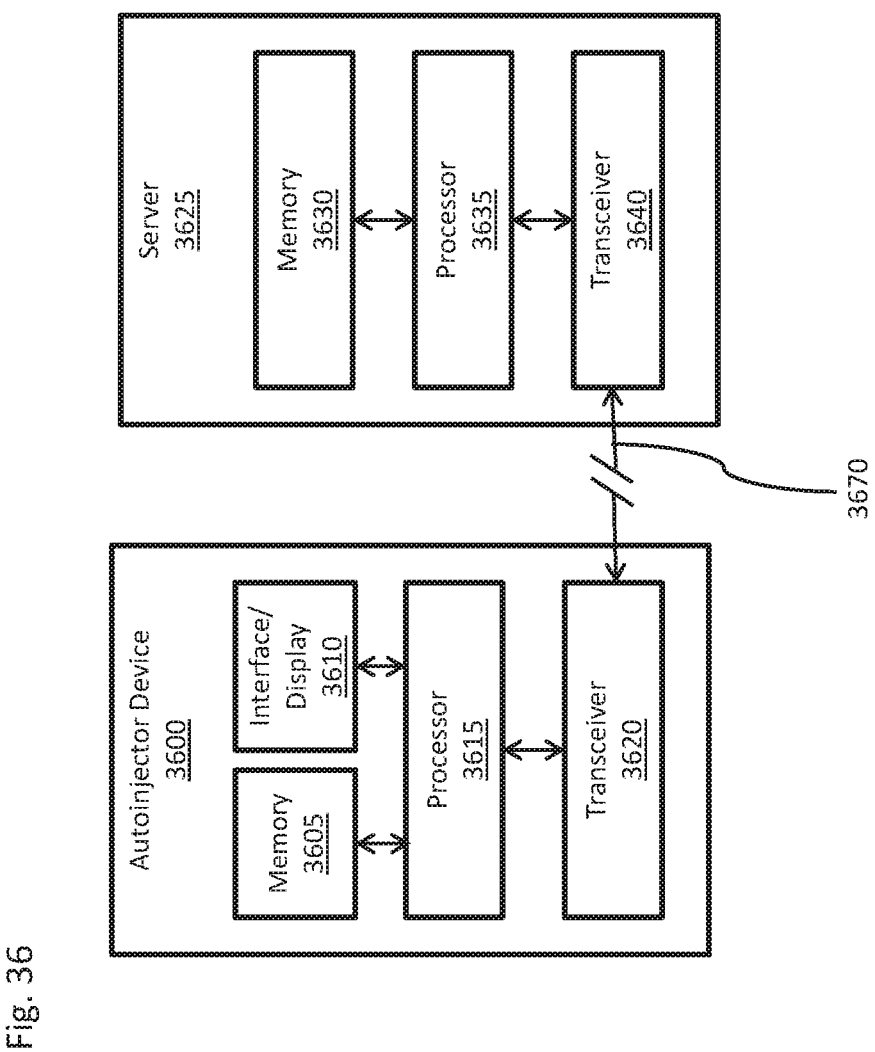
FIG. 36 is a block diagram illustrating an autoinjector and server computing devices in accordance with the disclosed embodiments.

FIG. 36 is a block diagram illustrating an autoinjector computing device 3600 and server computing device 3625 in accordance with the disclosed embodiments. The computing components shown in FIG. 36 may be used to implement the various methods and systems disclosed herein with respect to autoinjectors. For example, the autoinjector may be controlled by instructions stored on the memories of the server 3625 and or the autoinjector device 3600. In various embodiments, fewer, additional and/or different components may be used in a system.

FIG. 36 illustrates the autoinjector device 3600 and a server 3625 that may be used in accordance with various embodiments. The autoinjector device 3600 includes a processor 3615 that is coupled to a memory 3605. The processor 3615 can store and recall data and applications in the memory 3605, including applications that control and track aspects of autoinjectors as disclosed herein. The processor 3615 may also display objects, applications, data, etc. on the interface/display 3610. The processor 3615 may also receive inputs through the interface/display 3610. The processor 3615 is also coupled to a transceiver 3620. With this configuration, the processor 3615, and subsequently the first party autoinjector device 3600, can communicate with other devices, such as the server 3625 through a connection 3670.

The server 3625 includes a processor 3635 that is coupled to a memory 3630. The processor 3635 can store and recall data and applications in the memory 3630. The processor 3635 is also coupled to a transceiver 3640. With this configuration, the processor 3635, and subsequently the server 3625, can communicate with other devices, such as the first party autoinjector device 3600 through a connection 3670.

The devices shown in the illustrative embodiment may be utilized in various ways. For example, the connection 3670 may be varied. The connection 3670 may be a hard wired connection. A hard wired connection may involve connecting the devices through a USB (universal serial bus) port, serial port, parallel port, or other type of wired connection that can facilitate the transfer of data and information between a processor of a device and a second processor of a second device. In another embodiment, the connection 3670 may be a dock where one device may plug into another device. While plugged into a dock, the autoinjector device 3600 may also have its batteries charged or otherwise be serviced as well as upload information about medicament deliveries to a server. In other embodiments, the connection 3670 may be a wireless connection. The connection 3670 may take the form of any sort of wireless connection, including but not limited to Bluetooth connectivity, Wi-Fi connectivity, cellular data network connectivity (e.g., 3G, 4G, LTE, 5G), another wireless protocol, or any combination thereof. Other possible modes of wireless communication may include near-field communications, such as passive radio-frequency identification (RFID) and active (RFID) technologies. RFID and similar near-field communications may allow the various devices to communicate in short range when they are placed proximate to one another. In an embodiment using near field communication, two devices may have to physically (or very nearly) come into contact, and one or both of the devices may sense various data such as acceleration, position, orientation, velocity, change in velocity, IP address, and other sensor data. The system can then use the various sensor data to confirm a transmission of data over the internet between the two devices. In yet another embodiment, the devices may connect through an internet (or other network) connection. That is, the connection 3670 may represent several different computing devices and network components that allow the various devices to communicate through the internet, either through a hardwired or wireless connection. The connection 3670 may also be a combination of several modes of connection.

To operate different embodiments of the system or programs disclosed herein, the various devices may communicate in different ways. For example, the autoinjector device 3600 may download various software applications from the server 3625 through the internet. Such software applications may allow the various devices disclosed herein to perform some or all of the processes and functions described herein. In another embodiment, the autoinjector device 3600 may operate using internet browsers that can access websites that perform the functionality of any of the systems and methods disclosed herein. Additionally, the embodiments disclosed herein are not limited to being performed only on the disclosed devices in FIG. 36. It will be appreciated that many various combinations of computing devices may also communicate with an autoinjector and assist in executing the methods and systems disclosed herein. Examples of such computing devices may include smart phones, personal computers, servers, laptop computers, tablets, blackberries, RFID enabled devices, or any combinations of such devices.

The configuration of the devices in FIG. 36 is merely one physical system on which the disclosed embodiments may be executed. Other configurations of the devices shown may exist to practice the disclosed embodiments. Further, configurations of additional or fewer devices than the ones shown in FIG. 36 may exist to practice the disclosed embodiments. Additionally, the devices shown in FIG. 36 may be combined to allow for fewer devices or separated where more than the two devices shown exist in a system.

In some embodiments, systems and methods for automatically removing a needle cap may be implemented on any device/injector having a needle.

In some embodiments, systems and methods for automatically removing a needle cap may be implemented on an injector assembly for automatically delivering a dose of a medicament to a subject in a controlled manner. Such an injector assembly may include, for example, an activation switch for initiating automatic delivery of the dose of the medicament, a needle aperture at a distal end of the injector assembly and for enabling an injection needle to pass there through, a plunger drive mechanism for applying pressure to the plunger assembly, and a cavity for housing at least a portion of a removable cartridge module. The removable cartridge module may include (a) a needle housing for dictating the range of injection depths or possible, (b) a plunger housing for aligning a plunger assembly with the plunger drive unit, (c) an identification code associated with the medicament, and (d) a cavity for reversibly securing a pre-filled cartridge in the proper orientation.

In these embodiments, the removable cartridge module may be similar to the dose cassette described above, for example, with respect to FIGS. 11-14. Further, the injector assembly may include mechanisms for removing the needle cap similar to mechanisms describe above with respect to, for example, FIGS. 9-22. Thus, the removable cartridge module may include a needle cap 108 that may be automatically removed by the injector assembly.

In one embodiment, the pre-filled cartridge includes: (i) a barrel for containing the medicament and having a proximal end and a distal end, (ii) a needle operably connected to the distal end of the barrel, (iii) a plunger assembly including a plunger rod having a distal end initially located near the proximal end of the barrel, and a proximal end including a plunger head, and (iv) an amount of the medicament.

In one embodiment, the plunger drive mechanism includes a motor operably connected to the activation switch (e.g. a button, toggle, lever, dial, rocker or similar) and an actuator operably connected to the motor and the plunger assembly; at least one engagement feature for securing the removable cartridge module in the cavity in the proper orientation; a door, at least a portion of which is optionally substantially transparent, for enabling installation and/or removal of the removable cartridge module to/from the injector cavity, as well as loading and/or removal of the pre-filled cartridge to/from the installed cartridge module cavity; a cartridge module drive assembly for moving the cartridge module axially towards the proximal and distal end of the injector assembly, the cartridge module drive assembly including at least one gear element operably connected to the motor and the activation switch; a code reader for reading an identification code associated with the pre-filled cartridge and the medicament contained within the cartridge; a sensor for detecting contact with skin of the subject; a battery operably connected to the motor; a control unit (e.g. microcontroller) with associated memory containing a library of injection programs and operably connected to the sensors, code reader, drive mechanism(s) and activation switch.

In some embodiments, a cartridge module may include a needle housing for dictating the range of injection depths possible; a plunger housing for aligning a plunger assembly with the plunger drive unit; a cavity for reversibly securing a cartridge pre-filled with a medicament; an identification code associated with the pre-filled cartridge and the medicament contained within; at least one fitting for removably engaging the cartridge module with the injector assembly in the proper orientation; and at least one fitting for engaging the cartridge module with a cartridge module drive assembly, optionally wherein the cartridge drive assembly is integrated with the injector assembly.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An autoinjector device comprising:
a dose cassette comprising:
an outer container and
a needle cap having a base with a diameter larger than the outer container of the dose cassette;
a housing for receiving the dose cassette;
a clasp mechanism configured to secure the dose cassette within the housing upon insertion of the dose cassette into the housing; and
an actuator configured to move the dose cassette proximally within the housing after the dose cassette is secured within the housing, wherein:
the movement of the dose cassette causes the base of the needle cap to mechanically engage with a distal end of the housing, and
the mechanical engagement between the base of the needle cap and the distal end of the housing causes the needle cap to separate from the dose cassette.

2. The autoinjector device of claim 1, further comprising a sensor at the distal end of the housing configured to detect a presence of the base of the needle cap.

3. The autoinjector device of claim 2, wherein the sensor is further configured to detect that the needle cap has separated from the dose cassette.

4. The autoinjector device of claim 3, wherein the dose cassette comprises a medicament, and wherein the autoinjector device is configured to deliver the medicament after detecting that the needle cap has separated from the dose cassette.

5. The autoinjector device of claim 1, wherein the dose cassette further comprises an inner container configured to store a medicament.

6. An autoinjector device, comprising:
a dose cassette comprising:
an outer container and
a needle cap having a base with a diameter larger than the outer container of the dose cassette;
a housing for receiving the dose cassette;
a clasp mechanism configured to secure the dose cassette within the housing upon insertion of the dose cassette into the housing; and
an actuator configured to move the dose cassette proximally within the housing after the dose cassette is secured within the housing, wherein:
the movement of the dose cassette causes the base of the needle cap to mechanically engage with a distal end of the housing, and
the mechanical engagement between the base of the needle cap and the distal end of the housing causes the needle cap to separate from the dose cassette,
wherein the needle cap further comprises a needle shield portion sized to fit within a needle opening of the outer container of the dose cassette.

7. An autoinjector device of claim 1, comprising:
a dose cassette comprising:
an outer container and
a needle cap having a base with a diameter larger than the outer container of the dose cassette;
a housing for receiving the dose cassette;
a clasp mechanism configured to hold the dose cassette within the housing; and
an actuator configured to move the dose cassette proximally within the housing after the dose cassette is secured within the housing, wherein:
the movement of the dose cassette causes the base of the needle cap to mechanically engage with a distal end of the housing, and
the mechanical engagement between the base of the needle cap and the distal end of the housing causes the needle cap to separate from the dose cassette,
wherein the outer container of the dose cassette comprises a ledge and the clasp mechanism comprises a base latch configured to fix to the ledge and thereby secure the dose cassette within the housing.

8. The autoinjector device of claim 7, wherein a distal end of the base latch comprises a ramp surface and a locking surface, wherein during an insertion of the dose cassette, the outer container of the dose cassette is configured to mechanically engage with the ramp surface and push the distal end of the base latch radially outward until the distal end of the base latch reaches the ledge.

9. The autoinjector device of claim 8, wherein upon reaching the ledge, the distal end of the base latch moves radially inward into a space in the outer container of the dose cassette at the ledge.

10. The autoinjector device of claim 9, wherein the locking surface contacts the outer container at the ledge after the base latch moves radially inward into the space in the outer container.

11. The autoinjector device of claim 7, wherein the base latch is operably connected to the actuator, and the actuator is configured to move the dose cassette proximally within the housing by moving the base latch.

12. A method comprising:
receiving a dose cassette into a housing, wherein the dose cassette comprises an outer container and a needle cap having a base with a diameter larger than the outer container;
securing the dose cassette upon insertion of the dose cassette into the housing using a clasp mechanism;
moving the dose cassette proximally within the housing after the dose cassette is secured within the housing; and
separating the needle cap from the dose cassette because of mechanical engagement between a distal end of the housing and the needle cap.

13. The method of claim 12, further comprising:
sensing a presence of the base of the needle cap at the distal end of the housing,
wherein the dose cassette is moved proximally within the housing to separate the needle cap from the dose cassette only after the presence of the base of the needle cap is sensed at the distal end of the housing.

14. The method of claim 12, further comprising:
determining that the needle cap has separated from the dose cassette; and
delivering a medicament of the dose cassette only after determining that the needle cap has separated from the dose cassette.

15. The method of claim 12, wherein the outer container of the dose cassette comprises a ledge and the clasp mechanism comprises a base latch, and wherein the method further comprises securing the dose cassette within the housing by fixing the base latch to the ledge.

16. The method of claim 15, wherein:
a distal end of the base latch comprises a ramp surface and a locking surface, and
during an insertion of the dose cassette into the housing, the outer container of the dose cassette mechanically engages with the ramp surface and pushes the distal end of the base latch radially outward until the distal end of the base latch reaches the ledge.

17. The method of claim 16, wherein upon reaching the ledge, the distal end of the base latch moves radially inward into a space in the outer container of the dose cassette.

18. The method of claim 17, wherein the locking surface contacts the outer container.

19. The method of claim 15, wherein the moving of the dose cassette proximally within the housing occurs by moving the base latch proximally within the housing, wherein the base latch is operably connected to an actuator.

20. A dose cassette, comprising:
an outer container;
an inner container configured to store a medicament; and
a needle cap comprising a base with a diameter larger than the outer container of the dose cassette and a needle shield portion configured to fit within a needle opening of the outer container of the dose cassette,
wherein:
the outer container is configured to be inserted into a housing of an autoinjector and comprises a ledge configured to attach to a clasp mechanism of the autoinjector,
the base of the needle cap is configured to mechanically engage with a distal end of the housing, and
the needle cap is configured to separate from the outer container as a result of the mechanical engagement between the distal end of the housing and the base of the needle cap.

* * * * *